United States Patent [19]

Andrews et al.

[11] Patent Number: 4,826,816
[45] Date of Patent: May 2, 1989

[54] ANTIHYPERTENSIVE COMPOUNDS

[75] Inventors: David R. Andrews, Bloomfield; Federico C. A. Gaeta, Rockaway Township, Morris County, both of N.J.

[73] Assignee: Schering Corporation, Kenilworth, N.J.

[21] Appl. No.: 784,000

[22] Filed: Oct. 4, 1985

Related U.S. Application Data

[63] Continuation-in-part of Ser. No. 653,186, Sep. 24, 1984, Pat. No. 4,556,655, and Ser. No. 721,015, Apr. 8, 1985, Pat. No. 4,634,698.

[51] Int. Cl.[4] .............. A61K 37/00; A61K 31/54; C07D 279/00; C07D 285/00
[52] U.S. Cl. .................. 514/19; 514/223.2; 530/337; 530/800; 544/6; 544/13
[58] Field of Search ............. 514/223.2, 19; 544/13, 544/6; 530/337, 800

[56] References Cited

U.S. PATENT DOCUMENTS

| 4,431,644 | 2/1984 | Smith et al. | 544/13 |
| 4,468,396 | 8/1984 | Magatti | 544/13 |
| 4,536,501 | 8/1985 | Sundeen et al. | 514/225 |
| 4,616,012 | 10/1986 | Neustadt et al. | 514/223.2 |

FOREIGN PATENT DOCUMENTS 95584  12/1983  European Pat. Off. ............. 544/12

Primary Examiner—Douglas W. Robinson
Attorney, Agent, or Firm—Anita W. Magatti; Stephen I. Miller

[57] ABSTRACT

Antihypertensive compounds with angiotensin-converting enzyme inhibitory activity and diuretic activity are disclosed. Such compounds are useful in the treatment of cardiovascular disorders, especially hypertension and congestive heart failure, and are useful in the treatment of glaucoma.

25 Claims, No Drawings

4,826,816

ANTIHYPERTENSIVE COMPOUNDS

This application is a continuation-in-part of applications Ser. No. 653,186 filed Sept. 24, 1984, now U.S. Pat. No. 4,556,655 and Ser. No. 721,015, filed Apr. 8, 1985, now U.S. Pat. No. 4,634,698.

SUMMARY

The present invention relates to carboxyalkyl dipeptides joined through a sulfonamido group to a diuretic moiety. Compounds of this invention are useful as antihypertensive agents, in the treatment of congestive heart failure and in the treatment of glaucoma. In addition, compounds of this invention have diuretic and/or angiotensin converting enzyme inhibitory activity.

DETAILED DESCRIPTION

More particularly, this invention relates to compounds represented by the following formula I $$[D]-SO_2N-[B]-CH-[E]-CH-C-[A]-COR^8$$

with substituents $R^6$, $R^7$, $R^1$, $C=O$, $O$ (I)

and the pharmaceutically acceptable salts thereof, wherein:

A is structures IIa, IIb, IIc, IId, IIe l is 1 or 2;
n is 0 or 1;
p and q are 0, 1 or 2, provided that in structures IIb and IIc the sum of p and q is 1 or 2, and that in formula IId, p is not 0;

B is —[J]—[L]—[M]—;
D is structures IIIa, IIIb

E is —NH—, —O—, —S—, or —CH$_2$—;
G is $$-\overset{O}{\underset{\|}{C}}- \text{ or } -SO_2-;$$

J is —(CH$_2$)$_s$— or —((CH$_2$)$_r$—W)—;
L is a chemical bond, cis- or trans-lower alkene, lower alkyne, -Z-aryl-, -aryl-Z-, -Z-cycloalkyl-, -cycloalkyl-Z-, a 5- or 6-membered heterocyclic radical comprising 3 to 5 carbon atoms and 1 or 2 heteroatoms selected from N, O and S, or a $R^5$-substituted heterocyclic radical, wherein aryl is

[aryl structures with $R^5$]

and cycloalkyl is

[cycloalkyl structures with $R^5$ and (CH$_2$)$_w$]

wherein
w is 1, 2 or 3;
M is —(CH$_2$)$_u$— or —((CH$_2$)$_r$—X—(CH$_2$)$_v$)—;
W is $$-\overset{O}{\underset{\|}{C}}NH- \text{ or } -NH\overset{O}{\underset{\|}{C}}-;$$

X and Z are independently a chemical bond, $$-NR^9-, -O-, -S-, -\overset{O}{\underset{\|}{C}}NH- \text{ or } -NH\overset{O}{\underset{\|}{C}}-;$$

s, u and v are independently 0–5;
t is 1–5;
$R^1$, $R^2$ and $R^9$ are independently hydrogen, lower alkyl or lower acyl;
$R^3$ is hydrogen, lower alkyl, haloloweralkyl, phenylloweralkyl, (cycloalkyl)lower alkyl, aminomethyl, lower alkylaminomethyl, phenylloweralkylaminomethyl, or (cycloalkyl)loweralkylaminomethyl, loweralkylthiomethyl haloloweralkylthiomethyl, 2-, 3- or 4-pyridylloweralkyl, 2-, 4- or 5-thiazolyl-loweralkyl, 2-, 4- or 5-1H-imidazolylloweralkyl, 1-imidazolylloweralkyl, 1-morpholinoloweralkyl or hydroxyphenylloweralkyl;

$R^4$ is chlorine or $CF_3$;

$R^5$ is hydrogen, halogen, lower alkyl, lower acyl, lower alkoxy, haloloweralkyl or phenylloweralkyl;

$R^7$ is hydrogen, lower alkyl or aminoloweralkyl;

$R^6$ and $R^8$ are independently hydroxy, alkoxy having from 1 to 8 carbon atoms, benzyl, allyl, $R^{10}$—Q—,—$(CH_2)_m$—O—, wherein Q is oxygen or sulfur, r is O or 1 and m is 2 to 4,

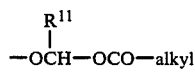

wherein the alkyl has from 3 to 8 carbon atoms,

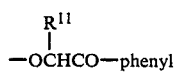

wherein the phenyl may be substituted with group T defined below, 1-glyceryl,

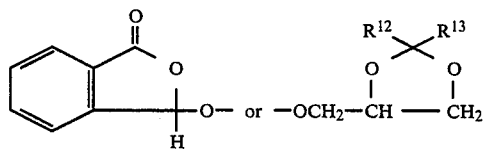

$R^{10}$ is phenyl, substituted phenyl wherein the substituents are chosen from group T, 1-naphthyl or 2-naphthyl;

T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;

$R^{11}$ is hydrogen or alkyl having from 1 to 8 carbon atoms;

$R^{12}$ is hydrogen, lwer alkyl, unsubstituted or substituted phenyl and substituted or unsubstituted phenyl lower alkyl wherein phenyl may be substituted by group T;

$R^{13}$ is hydrogen or lower alkyl;

provided that if L is alkene or alkyne, J is —$(CH_2)_s$— wherein s is 1-5; provided that if L is —Z-aryl-or —Z-cycloalkyl—, J is —$(CH_2)_s$— wherein s is 2-5; provided that if L is alkene, alkyne, —aryl—Z— or —cycloalkyl—Z—, M is —$(CH_2)_u$— wherein u is 1-5; provided that if s and u are each zero, L is aryl or cycloalkyl (i.e. Z is a bond); and provided that if s and v are each zero, L is aryl or cycloalkyl (i.e. Z is a bond);

with the further provision that when D is of formula IIIb and $R^1$ is hydrogen, B is not —$(CH_2)_4$—; and that when D is of formula IIIb and $R^1$ is hydrogen or lower alkyl, B is not —$(CH_2)_s$—aryl—$(CH_2)_t$—X—$(CH_2)_v$— wherein s is 0 or 1, t is 1, v is 0 to 2 and X is a bond, —O—, or —S—.

When A is formula IIb or IIc, the preferred sum of p and q is 1; when A is of formula IId, preferred values for p, q and n are 1,1 and zero, respectively. Preferably, A is IIa or IIb wherein p is zero and q is 1.

Preferred are compounds wherein D is of formula IIIa, with compounds wherein $R^4$ is chlorine and G is —$SO_2$— being more preferred. $R^2$ is preferably hydrogen and $R^3$ is preferably phenylethyl, (cyclopentyl)-methyl, chloromethyl, dichloromethyl, 2-pyridinylethyl, butyl, pentyl or trifluoroethylthiomethyl.

Also preferred are compounds wherein B is

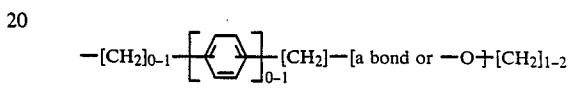

i.e., compounds wherein J is —$(CH_2)_s$— and s is 0-1, L is a bond or —aryl—Z— wherein Z is a bond and M is —$((CH_2)_t$—X-$(CH_2)_v)$, wherein t is 1, v is 1-2, and X is a bond or —O—.

For compounds wherein L is a heterocyclic radical, thiazolyl rings joined to the rest of molecule at the 2,4 and 2,5 positions are preferred.

A preferred group for E is —NH—.

Another group of preferred compounds are those wherein $R^7$ is hydrogen, methyl or aminobutyl. Preferred values for $R^6$ and $R^8$ are hydroxy, ethoxy, methoxy, phenoxyethoxy, 1-glyceryl, pivaloyloxyalkyloxy, and

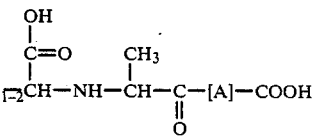

A preferred group of compounds are those represented by the general formula

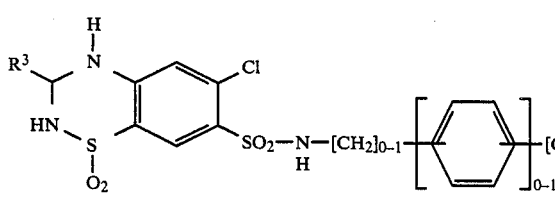

wherein $R^3$ is phenylethyl, chloromethyl, dichloromethyl, butyl, pentyl, (cyclopentyl)methyl, trifluoroethylthiomethyl or 2-pyridinylethyl.

As used herein, "lower alkyl" means straight or branched chain hydrocarbon radicals of from 1 to 6 carbons, e.g. methyl, ethyl, propyl, isopropyl, butyl, t-butyl, pentyl and hexyl. Similarly, "lower alkoxy" means straight or branched alkoxy radicals having from 1 to 6 carbon atoms, e.g. methoxy, ethoxy, propoxy, butoxy, isobutoxy, pentoxy and hexyloxy. "Halogen" means fluorine, chlorine and bromine. "Lower acyl" means organic radicals obtained by removing the hydroxyl group from the corresponding carboxylic acid of from 1 to 6 carbons, e.g. formyl, acetyl, propionyl and butyryl. "Lower alkene" means unsaturated hydrocarbon radicals of from 2 to 6 carbon atoms having one double bond, e.g. vinylene propenyl, butenyl, pentenyl and hexenyl, wherein the double bond may be present anywhere in the chain, e.g. 1-or 2-propenyl, 1-, 2- or 3-butenyl. Similarly, "lower alkyne" means a hydrocarbon radical of from 2 to 6 carbon atoms having one triple bond, e.g. ethynylene, propynyl, butynyl, pentynyl and hexynyl, wherein the triple bond may be present anywhere in the chain, e.g. 1- or 2-propynyl, 1-, 2- or 3-butynyl. Examples of heterocyclic radicals are:

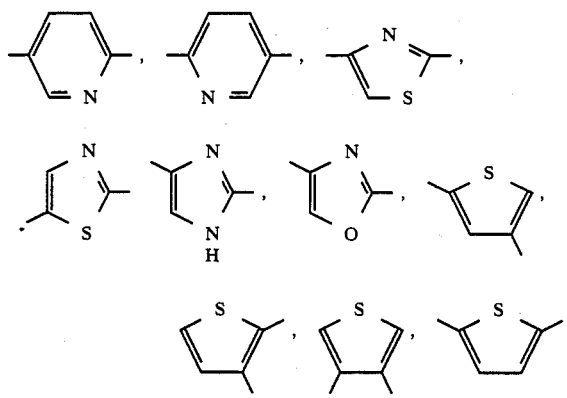

Compounds of the instant invention include various stereoisomers. Preferred stereoisomers are those in which the absolute configuration at carbon atoms adjacent to both a nitrogen and a carbonyl group corresponds most closely to the absolute configuration of L-amino acids.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic bases may be prepared, e.g., N-methylglucamine, lysine and arginine, as well as salts with organic and inorganic acids, e.g., HCl, HBr, $H_2SO_4$, $H_3PO_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

Compounds of formula I may be prepared by several routes using methods known in the art.

For example, compounds of formula I can be prepared by condensing an acid of formula IV (or its hydrochloride salt) with an amino acid derivative of formula V:

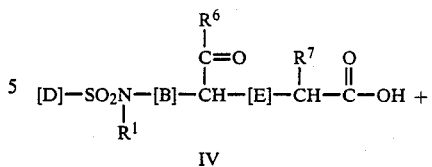

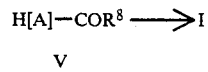

wherein $R^1$, $R^6$, $R^7$, $R^8$, D, B, E and A are as defined above. The reaction is carried out in an inert solvent such as dimethylformamide (DMF) in the presence a condensing agent such as 1-(3-dimethylaminopropyl)-3-ethyl carbodiimide hydrochloride (DEC) and 1-hydroxybenzotriazole, and where the compound of formula IV is a salt in the presence of a base such as triethylamine. The reaction is preferably carried out in an inert atomsphere at a temperature of 0°-25° C.

Compounds of formula V are known in the art, or may be prepared by methods well known to those skilled in the art.

Compounds of formula IV may be prepared for example from the reaction of a sulfonyl chloride of formula VI and an amine of formula VII:

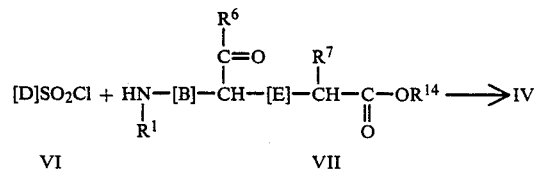

wherein D, B, E, $R^1$, $R^6$ and $R^7$ are as defined above and $R^{14}$ is a readily removable ester protecting group such as t-butyl, benzyl or trimethylsilylethyl. The reaction is carried out at 0°-5° C. in a solvent such as tetrahydrofuran (THF).

Compounds of formula VI may be prepared from known starting materials using procedures well known in the art. For example, when D is of the formula IIIa wherein G is $SO_2$ and $R^3$ is phenylethyl, the sulfonyl chlorides of formula VI may be obtained by reacting a disulfonyl chloride of formula VIII with aqueous ammonia at low temperature (dry-ice-acetone bath) in a solvent such as 1,2-dimethoxyethane (DME) in the presence of a base such as triethylamine to obtain a sulfonamide of formula IX, followed by reaction of the sulfonamide with phenyl propanal in a solvent such as DME and in the presence of an acid such as p-toluenesulfonic acid:

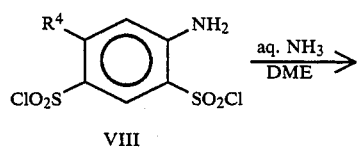

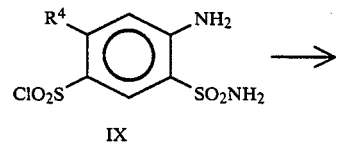

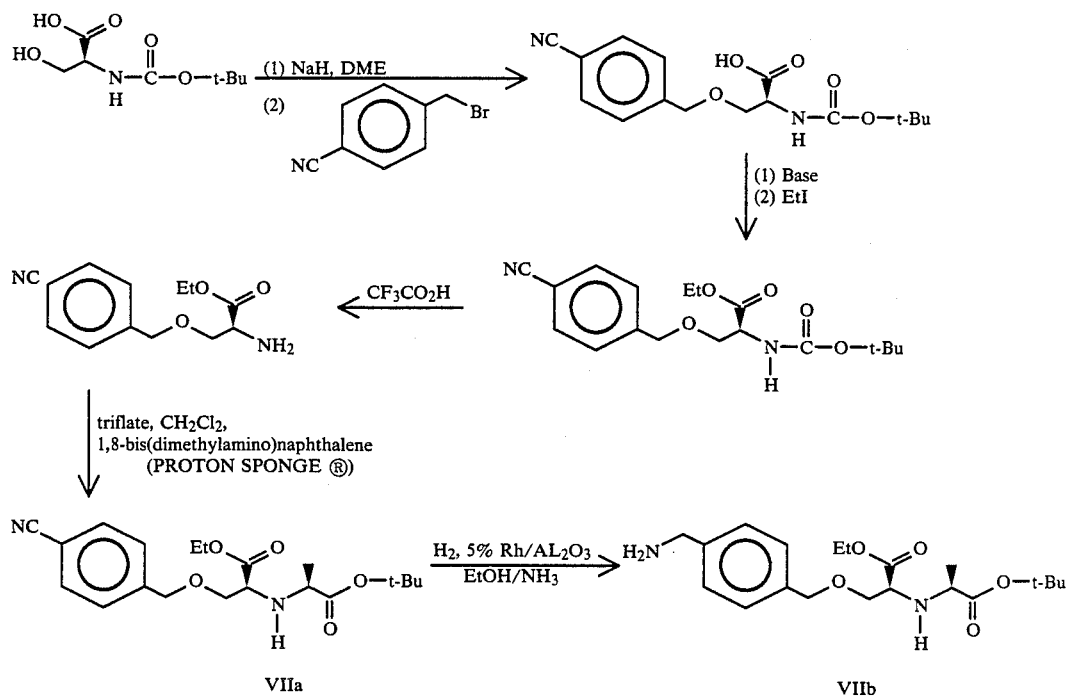

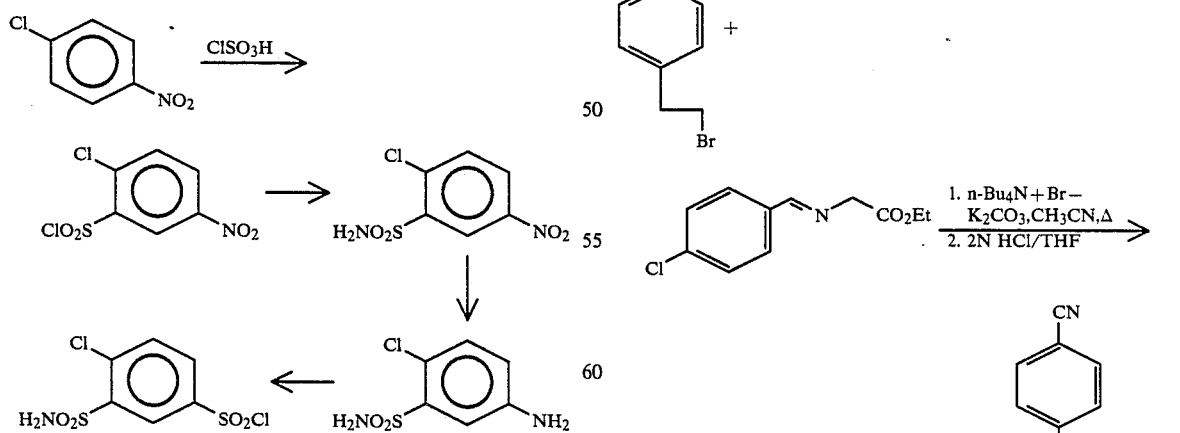

Details of the above typical reaction scheme are disclosed in Example 1, Parts A-E.

In the above reaction scheme, the triflate reagent, i.e. t-butyl 2(S)-(trifluoromethanesulfonyloxy)propionate, reacts by nucleophillic displacement with the α-aminoacid ester to give a high yield of the corresponding specific diastereomer of the resulting monoamino dicarboxylic acid ester.

Compounds of formula VIId, wherein M is $(CH_2)_2$ nd $R^1$, $R^6$, $R^7$, $R^{14}$, J, L and E are as described above or formula VIIb, may be prepared as follows:

Similarly, when D is of formula IIIb, the sulfonyl chlorides of formula VI may be obtained by well known procedures. A typical reaction scheme follows:

Compounds of formula VII are prepared from known starting materials using methods known in the art. A typical reaction scheme is shown below for compounds of formula VIIb, wherein $R^1$ is hydrogen, $R^6$ is lower alkyl, $R^7$ is methyl, J is —(CH$_2$)—, L is phenyl, M is —CH$_2$—O—CH$_2$—, E is —NH—, and $R^{14}$ is as defined above:

-continued

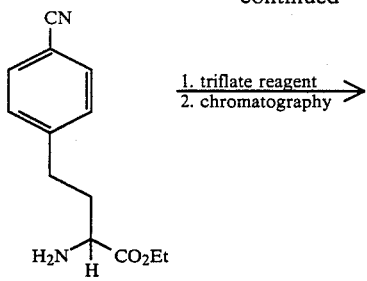

1. triflate reagent
2. chromatography

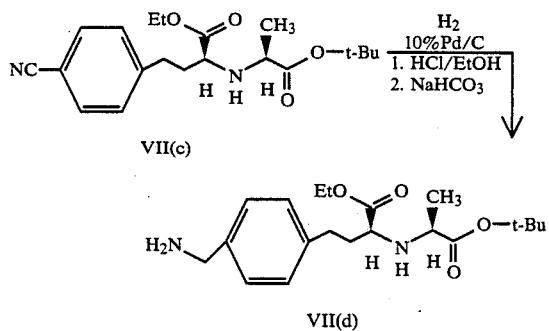

VII(c)

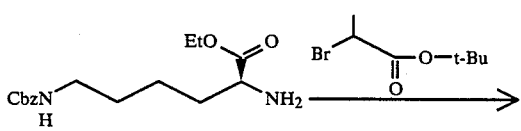

VII(d)

The above reaction scheme is exemplified in Parts A-C of Example 3.

A typical reaction scheme for the preparation of compounds of formula VIIf wherein L is a bond, J is —(CH$_2$)$_s$— and M is —(CH$_2$)$_u$)— wherein the sum of s and u is 4, and R$^1$, R$^6$, R$^7$, R$^{14}$ and E are as described above for formula VIIb is as follows:

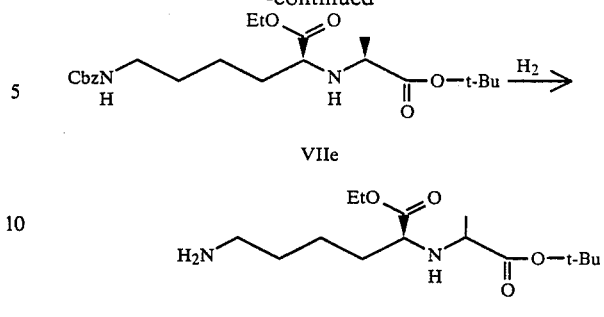

VIIe

VIIf

Example 5 provides details of this procedure.

Alternatively, intermediates of formulae VIIa or VIIc may be used to prepare compounds of formula I as follows: The R$^{14}$ protecting groups (e.g. t-butoxycarbonyl) of compounds of formulae VIIa or VIIc may be removed, e.g. by trifluoroacetic acid, and the nitrile reacted with an amino acid derivative of formula V under the conditions described on page 7. The resulting nitrile can then be reduced to the corresponding amine, e.g., by hydrogenation, which amine can then in turn be coupled to a sulfonyl chloride of formula VI by conventional ethods. Similarly, intermediates of formula VIIe (i.e., compounds of formula VII wherein B is alkyl) may be deprotected at the carboxylic acid group and condensed with the amino acid derivative of formula V as described above, then deprotected at the amino group, e.g. by hydrogenation, and the resultant amine reacted with a sulfonyl chloride of formula VI by conventional methods.

Another method for preparing compounds of formula IV is that exemplified below for preparing compounds wherein D is of formula IIIa wherein G is —SO$_2$—, J is —CH$_2$—, L is —aryl-Z— wherein aryl is phenyl and Z is

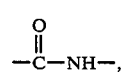

M is —CH$_2$—, E is —NH—, R$^1$ is hydrogen, R$^6$ is ethyl, R$^7$ is methyl, and R$^2$, R$^3$ and R$^4$ are as defined above:

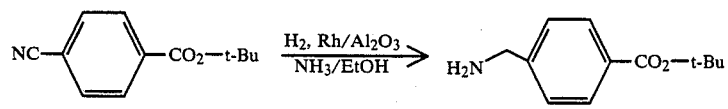

[D]SO$_2$Cl
(wherein G is —SO$_2$—)
(i-Pr)$_2$NEt

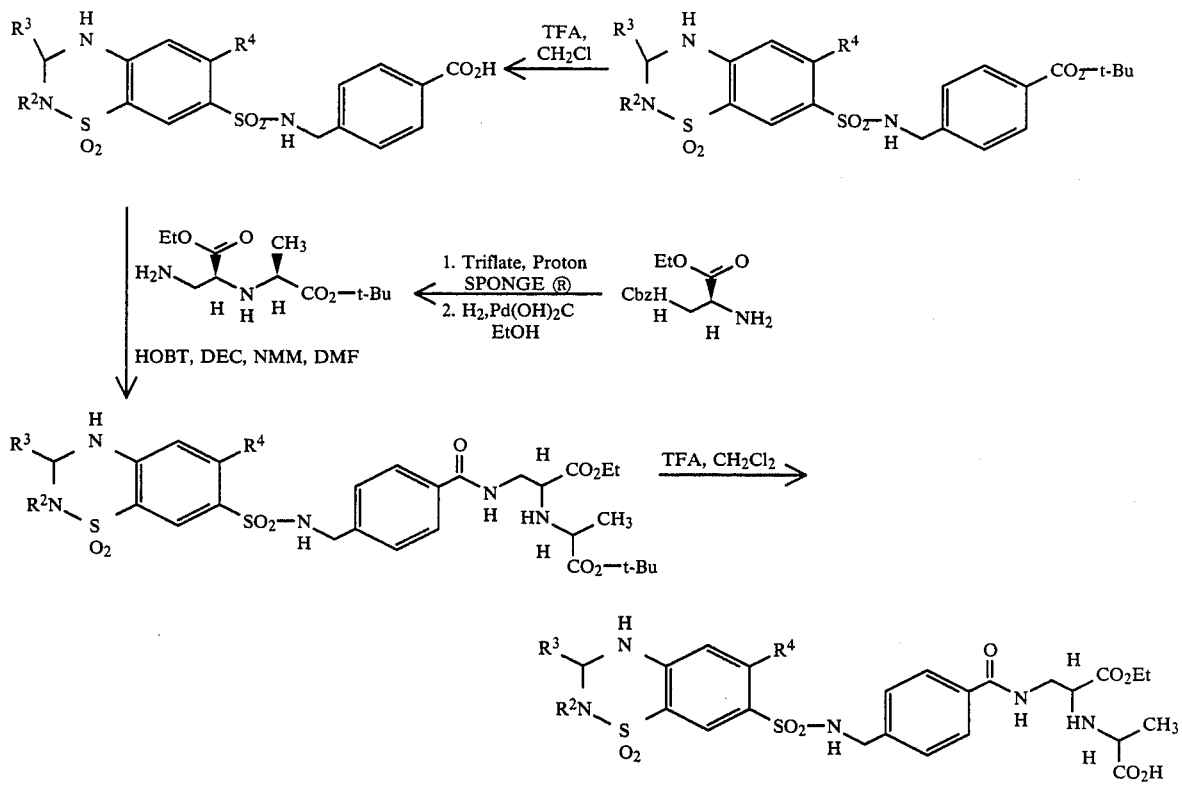

Example 7 incorporates the above procedure.

Another method for the preparation of compounds of formula I involves the sulfonylation of an amine of formula X with a sulfonylchloride of formula VI:

$$VI + HN-[B]-\overset{R^6}{\underset{R^1}{\overset{|}{C}}}H-[E]-\overset{R^7}{\underset{|}{C}}H-\overset{O}{\underset{\|}{C}}-[A]-COR^8 \longrightarrow I$$

X wherein $R^1$, $R^6$, $R^7$, $R^8$, B, E and A are as defined above. The reaction is carried out in an inert solvent such as THF in the presence of a proton acceptor such as N-methylmorpholine. The reaction is preferably carried out in an inert atmosphere at a temperature of 0-25<C.

Compounds of formula X may be prepared by well known methods, for example to obtain compounds wherein B is —CH$_2$—C$_6$H$_5$—(CH$_2$)$_2$—, E is —NH— and $R^1$, $R^6$, $R^7$ and $R^8$ are as defined above, compounds of formula VII(c) may be deprotected at the terminal carboxy group and then condensed with an amino acid of formula V:

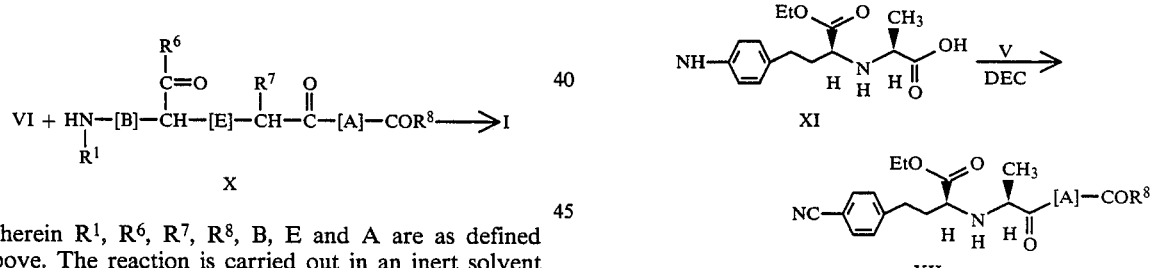

The nitrile of formula XII is reduced to an amine of formula X, e.g. by hydrogenation.

Compounds of formula I may also be prepared by condensing an aldehyde of formula XIII (or a reaction derivative thereof, e.g., an acetal) with an aminosulfonamide of formula XIV:

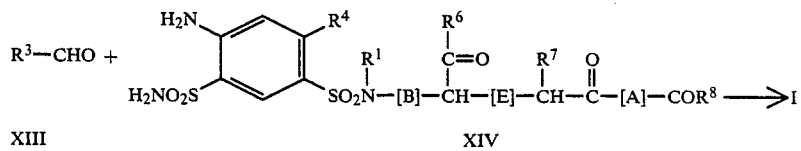

wherein $R^1$, $R^3$, $R^4$, $R^6$, $R^7$, $R^8$, B, E and A are as defined above. The reaction is carried out in an inert solvent such as THF in the presence of p-toluenesulfonic acid. The reaction is preferably carried out in an inert atmosphere at a temperature of 0°-80° C.

Compounds of formula XIII are known in the art or may be prepared by known methods.

Compounds of formula XIV can also be prepared by known methods, for example a sulfonamide of formula IX can be reacted with an amine of formula VII to obtain a compound of formula XV:

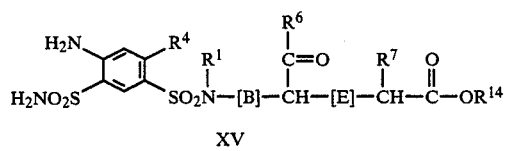

wherein $R^1$, $R^4$, $R^6$, $R^7$, $R^{14}$, B and E are as defined above. The protecting group $R^{14}$ is then removed e.g., by treating with hydrochloric acid in a solvent such as dioxane. The resultant product is condensed with an amino acid of formula V under conditions similar to those described above for the reaction of compounds of formulae IV and V to obtain a compound of formula XIV.

Yet another process for the preparation of the compounds of the formula I wherein X is sulfur comprises condensing a halide of the general formula XV

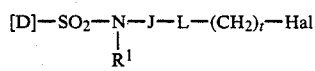

with a thiol of the general formula XVI

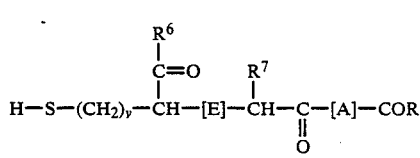

where $R^1$, $R^6$, $R^7$, $R^8$, A, E, J, L, t and v are as defined for formula I and Hal represents halogen, preferably bromine. The reaction is preferably carried out in an inert medium at a temperature of 0°–25° C.

Compounds of the formula XV may be prepared by well known methods. Illustrative of such methods, is the following specific reaction scheme:

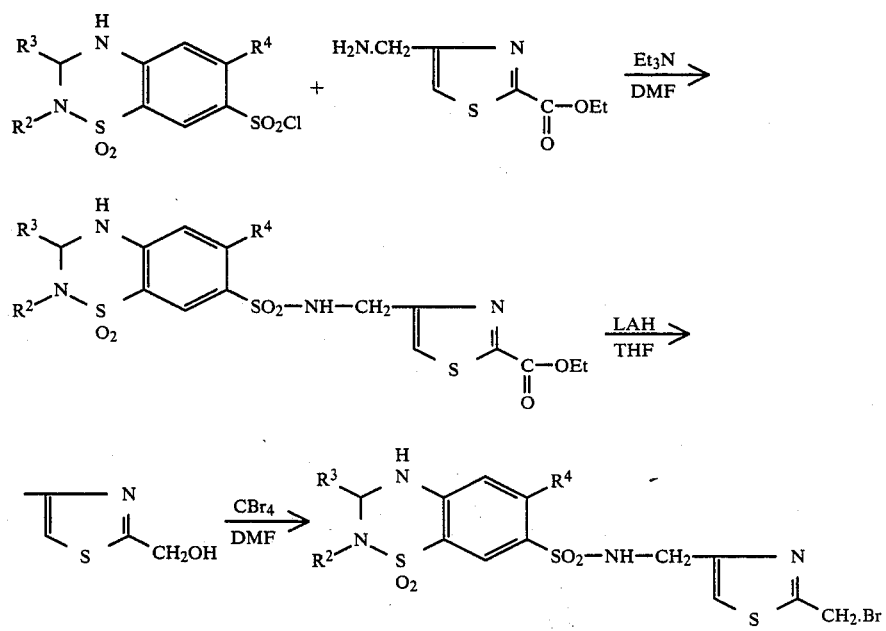

XV (wherein D is IIIa wherein G is $SO_2$,
J is $-(CH_2)_s-$ wherein 5 is 1,
L is 2-thiazolyl, t is 1,
$R^1$ is hydrogen, and Hal is bromine)

Compounds of general formula XVI may also be prepared by known methods, the following specific reaction scheme being illustrative of such methods:

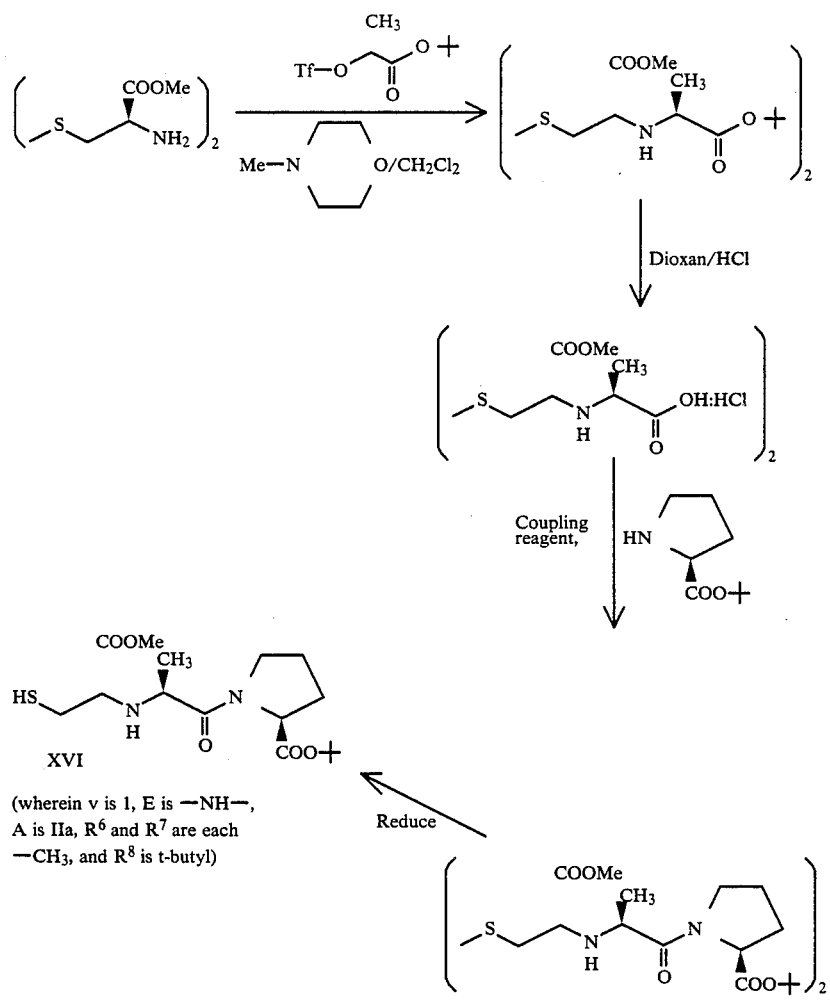

The known coupling methods above include amino group protection during the coupling reaction, for example with protecting groups such as N-formyl, N-t-butoxycarbonyl (t-Boc) and N-carbobenzyloxy (Cbz) groups, followed by their removal to yield compounds of formula I. Furthermore, the $COR^8$ function wherein $R^8$ is OH may be protected by removable ester groups such as benzyl, ethyl, t-butyl, trimethylsilylethyl and the like.

The more complex esters at $R^6$ (i.e., $R^6$ is other than hydroxy or alkoxy) are most conveniently prepared by esterifying compounds compounds of formula I wherein $R^6$ is hydroxy and $R^8$ is a protected hydroxy, e.g. benzyloxy, with the appropriate reagents, e.g. chloromethyl pivalate in the presence of base, to obtain the corresponding pivaloyloxymethyl ester; the benzyl group is then removed by conventional means, e.g. catalytic hydrogenation.

The following procedures and examples further illustrate the preparation of compounds of this invention.

PREPARATION 1 t-BUTYL 2(S)-(TRIFLUOROMETHANESULFONYLOXY)-PROPRIONATE (Triflate Reagent)

A. Add 2(S)-(p-toluenesulfonyloxy)propionic acid (4.4 g) to a cold solution of 10ml of isobutylene and 0.4 ml of concentrated sulfuric acid in 30 ml of methylene chloride in a pressure vessel, seal, and agitate at room temperature for 48 hours. Pour into 50 ml of 15% sodium carbonate solution, dry over magnesium sulfate and concentrate to obtain t-butyl 2(S)-(p-toluenesulfonyloxy)propionate as an oil (NMRδ1.37). Distilled material (Kugelrohr, 120°) has $[\alpha]D^{26} = -45.9°$ (EtOH, c=1).

B. Combine the product of part A (100 g) with acetic acid (40.0 g) and triethylamine (67.2 g) in 200 ml of dry DMF. Heat at 65° for 20 hours. Partition with 21 each ether and water, and wash the ether with citric acid, then with dilute sodium bicarbonate soultion. Dry and concentrate the ether solution to obtain t-butyl 2(R)-acetoxypropionate as a colorless liquid, bp 50° C./0.1 mm.

C. Combine the product of part B (62,6 g) with ethylenediamine (11.6 g) and heat at 70° for 24 hours. allow to cool, add 300 ml ether and filter. Wash the ether with water, 10% citric acid, and then with sodium bicarbonate solution. Dry and concentrate the ether solution to leave a colorless oil. Crystallize from hexane at −20° to give t-butyl 2(R])-hydroxypropionate as white needles, m.p. 41°-2° C.

D. Combine the product of part C (10 g) with pyridine (6 ml) in 100 ml methylene chloride. Cool to −70° C., and add dropwise over a period of about 45 minutes a solution of trifluoromethanesulfonic anhydride (13.5 g) in 20 ml methylene chloride, maintaining the temperature below −15° C. Stir at −20° C. for 30 min. Add ether and wash successively with water, 4 of aq HCl, sat'd NaHCO$_3$ and brine. Dry and concentrate the organic layer to obtain the title compound.

PREPARATION 2

6-CHLORO-3,4-DIHYDRO-3-(2-PHENYLETHYL)-2H-1,2,4-BENZOTHIADIAZINE-7-SULFONYL CHLORIDE 1,1-DIOXIDE

A. Dissolve 5 g 2-chloroaniline-3,5-disulphonyl chloride in 20 ml DME, cool to in a dry-ice/acetone both and add 2 ml triethylamine. Add dropwise 25% ammonium hydroxide in water (1 ml) in DME (4 ml), stir at in a dry-ice acetone bath for 1 hour, allow to warm to room temperature, and stir for 90 min. Dilute the resultant reaction mixture with ethyl acetate, wash with 4% aq HCl, water and brine, dry over MgSO$_4$ and evaporate to obtain a solid residue.

B. Combine 13.6 g of the sulfonamide prepared in Step A, 6.57 g phenyl propanal, 25 ml DME and 20 mg p-tolulenesulfonic acid and stir at room temperature under N$_2$ for 3 hours. Evaporate the solvent, dissolve the resultant residue in 250 ml ethyl acetate, wash with 100 ml sat'd aq. NaHCO$_3$, and 100 ml brine, then dry over MgSO$_4$, filter and evaporate the solvent to obtain the crude title compound. Purify the crude residue by precipitation in CH$_2$Cl$_2$; mp. 167.0°–167.5° C.

PREPARTION 3

CIS,SYN-OCTAHYDROINDOLE-2(S)-CARBOXYLIC ACID, t-BUTYL ESTER

A. Dissolve the product of Preparation 4 (77 g) in absolute ethanol (900 ml), add 5% Pd/C (10 g) and hydrogenate at room temperature at an initial pressure of 60 p.s.i. After 3 hours, filter off the catalyst and wash with hot methanol. Evaporate the combined filtrate and wash in vacuo, triturate the resultant residue in ethanol (100 ml), chill the solution, then filter and air dry the resultant precipitate to obtain a residue, m.p. 269°–270° C.

B. Suspend the product of Part A in dioxane (400 ml) and conc. H$_2$SO$_4$ (40 ml), add isobutylene (300 ml) and shake in a Parr shaker for 28 hours. Pour the resultant reaction mixture into 50% aqueous NaOH (150 ml) in 500 ml ice water and extract with ethyl ether (3×500 ml). Wash the combined organic extracts with water, then brine. Dry the the organic layer over Na$_2$SO$_4$ and evaporate the solvent to obtain the title compound.

PREPARATION 4

CIS,SYN-OCTAHYDROINDOLE-2(S)-CARBOXYLIC ACID BENZYL ESTER

A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g 10-d-camphorsulfonic acid in 1 liter of warm ethyl acetate and add a soultion of 86 g of the product of part A in 1 liter of ethyl acetate. Allow the mixture to crystallize, heat to reflux, cool to room temperature, and filter. Recrystallize the filter cake from a mixture of 500 ml isopropanol and 1800 ml ethyl acetate, filter and dry the crystals to obtain 2-(S)-carboethoxy-cis,syn-octahydroindole, d-10-camphorsulfonate, m.p. 192°–193° C.

C. Heat the product of Part B (107.6 g) and d-10-camphor-sulfonic acid (6.35 g) in benzyl alcohol (270 ml) at 105° C. under vacuum for 6 hours or until TLC (silica, elute neutralize sample with ethyl ether) indicates reaction is complete. Pour the resultant residue into ethyl ether, seed and stir to obtain a precipitate. Filter the precipitate, wash with ethyl ether (2×500 ml) and dry the resultant residue under vacuum to obtain 2-(S)-benzyloxy-cis, syn-octahydro-indole, d-10-camphorsulfonate, m.p. 114°–118° C.

D. Suspend the product of Part C (150 g) in ethyl ether (1500 ml), add 1N aqueous NaOH (300 ml) and stir until the solid dissolves. Separate the organic layer and wash the aqueous layer with ethyl ether (2×200 ml). Combine the organic layer, wash with brine, dry over Na$_2$SO$_4$ and evaporate the solvent to obtain the title compound.

PREPARATION 5

6-CHLORO-3,4-DIHYDRO-3-(CHLOROMETHYL)-2H-1,2,4-BENZOTHIADIAZINE-7-SULFONYL CHLORIDE 1,1-DIOXIDE

A. Dissolve the sulfonamide prepared in Part A of Preparation 2 (20 g) in dry DME (100 ml), add chloroacetaldehyde dimethyl acetal (10 ml) and p-toluenesulfonic acid and reflux for 3 hours or until TLC (silica, 3% ethyl acetate in CH$_2$Cl$_2$) indicates reaction is complete. Evaporate the solvent, dissolve the resultant residue in ethyl acetate, wash with saturated NaHCO$_3$, then brine and concentrate to half volume. Refrigerate overnight, filter the resultant precipitate, wash in hexane, filter and dry to obtain the title compound.

EXAMPLE 1

1-[2-(S)-[[1-(S)-CARBOETHOXY-2-[4-[[[6-CHLORO-3,4-DIHYDRO-3-(2-PHENYLETHYL)-2H-1,2,4-BENZOTHIADIAZIN-7-YL]SULFONYLAMINO]METHYL]PHENYLMETHOXY]ETHYL]AMINO]-1-OXOPROPYL]-[2S-[2α, 3aα, 7aα]]-OCTAHYDRO-1H-INDOLE-2-CARBOXYLIC ACID, S,S-DIOXIDE

A. To 10.4 g NaH (50% in mineral oil, washed with hexane) in 50 ml DMF at 0°–5° C., add dropwise over a 1 hour period 20 g of N-a-t-butoxycarbonyl-L-serine in 350 ml DMF. Stir at room temperature for 1 hour, then at 45° for 1 hour. Cool the reaction mixture to 0°–5° C. and add dropwise over 30 minutes 21.3 g of p-cyanobenzylbromide in 100 ml DMF. Stir at 0° C. for 80 minutes, add 30 ml water, stir and filter. Concentrate the filtrate and partition between ethyl acetate and sat'd. aq. NaHCO$_3$/H$_2$O. Wash the aqueous phase with ethyl acetate, adjust to pH 7.5 with 6N HCl and concentrate to approximately 100 mls.

B. To the product of Step A, add 60 ml methanol, 40 ml ethyliodide, and 4 g NaHCO$_3$. Stir under a nitrogen atomsphere for 72 hours, evaporate the solvent in vacuo and partition the residue between 800 ml ethyl acetate and 800 ml water. Separate the organic layer, and extract the aqueous layer with ethyl acetate; combine the organic extracts, wash with brine, dry over MgSO$_4$, filter and evaporate the solvent. Purify the resultant residue by High Pressure Liquid Chromatography (HPLC) using 2 Prep 500 cartriges and eluting with 21% ethyl acetate in hexane. Combine the desired fractions and evaporate the solvent to obtain a residue. FAB mass spec m/e=349 (M+H).

C. Cool 2 g of the product of Step B to 0°–5° C. and add dropwise 25 ml trifluoroacetic acid. Let stand until TLC (silica, elute with hexane:ethyl acetate) indicates no starting material is left. Add ethyl acetate, then evaporate the solvent in vacuo. Dissolve the resultant residue in ethyl ether, and wash with 1N aqueous NaOH; backwash the aqueous phase with ether, combine the ethereal extracts, dry over $K_2CO_3$ and evaporate the solvent to obtain a residue.

D. Cool 1.6 g triflate reagent (Preparation 1) in 10 ml $CH_2Cl_2$ to 0° C. Add dropwise 1.1 g of the product of Step C and 1.2 g of PROTON SPONGE® (1,8-bis(dimethylamino)naphthalene, Aldrich Chemical Co., Milwaukee, Wis.) in 20 ml $CH_2Cl_2$. Monitor reaction by TLC, adding 1,8-bis(dimethylamino)naphthalene and triflate reagent as necessary. Filter the resultant precipitate with the aid of ethyl acetate, evaporate the solvent, and purify the resultant residue by column chromatography, eluting with 30% ethyl acetate in hexane. FAB mass spec m/e=377 (M+H).

E. Dissolve 2.5 g of the product of Step D in 50 ml ethanol saturated with $NH_3$, add 1.25 g 5% $Rh/Al_2O_3$ and hydrogenate at 60 psi for 4 hours. Filter the resultant mixture through celite with the aid of ethanol, then evaporate the solvent in vacuo to obtain a residue.

F. Cool to 0° C. 2.5 g of the product of Step E in 25 ml dry THF and add dropwise 3.3 g 6-chloro-3,4-dihydro-3-(2-phenylethyl)-2H-1,2,4-benzothiadiazine-7-sulfonyl chloride 1,1-dioxide in 20 ml dry THF. Stir at 0° C. for 1 hour, then add 0.6 ml N,N-diisopropylethylamine and stir at room temperature for 2 hours. (Reaction may be monitored by TLC [silica; elute with hexane: ethyl acetate]). Add the reaction mixture to ethyl acetate, wash with 4% aq. HCl, sat'd $NaHCO_3$ and brine, then dry over $MgSO_4$ and evaporate the solvent in vacuo. Purify the resultant residue by HPLC: dissolve the residue in acetone:ethyl acetate:hexane (20:35:45) and separate on 2 Prep 500 cartridges using acetone:ethyl acetate:hexane (5.5:36.5:58) as mobile phase. Monitor eluent by TLC (silica; elute with acetone:ethyl acetate:hexane [6:39:55]), combine the desired fractions and evaporate the solvent in vacuo to obtain a residue. FAB mass spec m/e=766 (M+H).

G. Stir 2.9 g of the t-butyl ester of Step F in 40 ml HCl/dioxane overnight; pass nitrogen through the solution to evaporate the solvent and obtain the free acid.

H. Dissolve 2.9 g of the product of Step G in 6 ml DMF, add 1.1 g cis,syn-octahydro-1H-indole-2(S)carboxylic acid, t-butyl ester and 700 mg 1-hydroxybenzotriazole. Cool to 0° C., add 0.7 ml triethylamine and 900 mg 1-(3-dimethylaminopropyl)-3-ethyl carbodiimide hydrochloride and stir overnight. Evaporate the solvent in vacuo, take up the residue in ethyl acetate, and wash with water, 4% aq. HCl, sat'd aq. $NaHC_3$, and brine. Dry the organic layer over $MgSO_4$, filter and evaporate to obtain a residue.

Purify said residue by HPLC using 2 Prep 500 cartridges and methanol:ethyl acetate:hexane (5.25:36:58.75) as mobile phase (residue dissolved in methanol:ethyl acetate:hexane [10:35:55]). Combine the desired fractions as determined by TLC and evaporate the solvent. Rechromatograph the resultant residue by HPLC using acetone:ethylacetate:hexane (10:40:50) as mobile phase, combining the desired fractions and evaporating the solvent to yield the title compound as a t-butyl ester. FAB mass spec m/e=917 (M+H).

I. Stir 1.5 g of the product of Step H in 20 ml dioxane saturated with HCl overnight; pass nitrogen through the solution to evaporate the solvent. Purify the resultant residue on Dowex Ag 50 2X ($H^+$ form), eluting with (ethanol:water [1:1]):pyridine (95:5). Combine desired fractions as determined by TLC (silica; $CH_2Cl_2$:MeoH:AcOH [90:5:3]) and evaporate the solvent to obtain the title compound. FAB mass spec m/e=861 (M+H).

EXAMPLE 2

1-[2-(S)-[[1-(S)-CARBOXY-2-[4-[[[6-CHLORO-3,4-DIHYDRO-3-(2-PHENYLETHYL)-2H-1,2,4-BENZOTHIADIAZIN-7YL]SULFONYLAMINO]METHYL]PHENYLMETHOXY]ETHYL]AMINO]-1 OXOPROPYL]-[2S-(2α, 3aα, 7aα)]-OCTAHYDRO-1H-INDOLE-2-CARBOXYLIC ACID, S,S-DIOXIDE.

A. Treat the product of Example 1, Step G in a manner similar to that described in Example 1, Step H, first paragraph, substituting cis,syn-octahydro-1H-indole-2(S)-carboxylic acid, benzyl ester camphorsulfonate salt (see Preparation 4, Part C) for the t-butyl ester.

Purify the resultant residue by column chromatography on 100 g silica eluted with $CHCl_3$: ethyl acetate. Combine the desired fractions as determined by TLC (silica; elute with $CH_2Cl_2$:methanol:acetone [93:2:5]) and evaporate the solvent to obtain a residue. Further purify the residue on a sephadex column (350 g). FAB mass spec m/e=951 (M+H).

B. Suspend 450 mg of the diester obtained in Step A in 2 ml water. Add 2 ml 1N aq. NaOH and stir overnight at room temperature. Adjust to pH 6–7 with 1N HCl, filter the resultant solid and dry under vaccum to obtain the title compound. FAB mass spec m/e=833 (M+H).

EXAMPLE 3

1-[2-(S)-[[3-[4-[[[6-CHLORO-3,4-DIHYDRO-3-(2-PHENYLETHYL)-2H-1,2,4-BENZOTHIADIAZIN-7-YL]SULFONYLAMINOMETHYL]PHENYL]-1-(S)-(ETHOXYCARBONYL)PROPYL]AMINO]-1-OXOPROPYL]-[2S-(2α, 3aα, 7aα]-OCTAHYDRO-1H-INDOLE-2-CARBOXYLIC ACID, S,S -DIOXIDE HYDROCHLORIDE

A. 2-Amino-4-(4-cyano)phenylbutanoic acid, ethyl ester

Reflux 2-(4-cyano)phenylethyl bromide (23 gm), the p-chlorobenzaldimine of ethyl glycinate (21 gm), tetra-n-butylammonium bromide (10 gms) and freshly ground fine potassium carbonate powder (42 gms) in acetonitrile (150 mls) with mechanical stirring under nitrogren for 12 hours.

Cool the mixture, filter off the solid and wash the filter cake with ethyl acetate (3×150 mls). Wash the combined filtrate with water (2×100 mls) and evaporate the solvent in vacuo. Stir the residue vigorously with THF (200 mls) and 2N HCl (200 mls) at room temperature for 2 hours. Wash the aqueous phase with ethyl acetate, basify with solid potassium carbonate to pH 9 and extract with ethyl acetate to give the title compound of Part A.

B.

N-[1-(S)-(Ethoxycarbonyl)-3-(4-cyano)phenyl]-(S)-alanine, t-butyl ester

Slowly add the product of Part A (9 gms) and PROTON SPONGE ® (17.2 gm) in dry dichloromethane (80 mls) dropwise into a stirred solution of triflate reagent (22 gm) in dry dichloromethane (40 mls) cooled in an acetone-ice bath. Stir at room temperature overnight. Filter the resultant precipitate and wash the filter cake with ethyl acetate (5×100 ml). Wash the combined filtrate with 10% citric acid (3×100 ml); sodium bicarbonate (sat'd, 2×100 ml), and saturated brine (2×100 ml). Dry the solution over potassium carbonate in the presence of triethyl amine (5 mls), and remove the solvent in vacuo. Chromatograph the resultant residue (hexane:EtOAc:CH$_2$Cl$_2$ [8:1:1], 1% Et$_3$N; 500 gm silica gel; 230–400 mesh) to obtain the title compound of Part B.

C.

N-[3-(4-Aminomethyl)phenyl-1-(S)-(ethoxycarbonyl) propyl]-(S)-alanine, t-butyl ester Hydrogenate a mixture of the product of Part B (2 g), hydrogen chloride (0.2 gm) and 10% Pd/C (0.4 gm) in absolute ethanol (100 ml) at 50 psi for 5 hours. Filter the resultant mixture through celite. Evaporate the solvent to obtain the hydrogen chloride salt of the title compound of Part C.

D. Add N-methylmorpholine (0.5 ml) to a solution of the product of Part C (1 gm) in dry THF (20 mls) cooled in acetone-ice bath (−5° C.). Add the sulfonyl chloride of Preparation 2 (1.3 gm) and stir the resulting mixture at room temperature overnight. Dilute the resultant reaction mixture with ethyl acetate (400 ml), wash with 0.5N HCl (100 ml), saturated NaHCO$_3$ (2×100 ml), and brine (2×100 ml). Dry the solution over MgSO$_4$ and remove the solvent in vacuo. Purify the resultant residue by chromatography [400 gm silica gel, 230–400 mesh; first hexane:EtOAc:CH$_2$Cl$_2$, 4:1:1, then hexane:EtOAc:CH$_2$Cl$_2$, 1:1:1] to obtain a residue.

E. Add the product of Part D (1.76 gm) to 5.5 M HCl in dioxane (50 ml) and stir the resulting mixture at room temperature overnight. Evaporate the solvent in vacuo, triturate the solid residue with ether, and remove the solvent in vacuo to obtain a residue (hydrogen chloride salt).

F. Treat the product of part E in a manner similar to that described in Example 1, Part H, first paragraph, substituting N-methylmorpholine for triethylamine to obtain a residue. Purify the resultant residue by chromatography [400 gm silica gel 230–400 mesh; hexane:EtOAc:CH$_2$Cl$_2$, 1:2:1] to obtain the t-butyl ester of the title compound.

G. Stir the product of Part F (0.9 gm) in 5.5 M HCl/dioxane (40 mls) at room temperature for 2 hours. Remove the solvent in vacuo, triturate the product with ether, and dry in vacuo to obtain the title compound of Example 3.

EXAMPLE 4

1-[2-(S)-[[1-(S)-CARBOXY-3-[4-[[[6-CHLORO-3,4-DIHYDRO-3-(2-PHENYLETHYL)-2H-1,2,4-BENZOTHIADIAZIN-7-YL]SULFONYLAMINO]-METHYL]PHENYL]-PROPYL]AMINO]-1-OXO-PROPYL]-[2S-(2α,3aα,7aα)]-OCTAHYDRO-1H-INDOLE-2-CARBOXYLIC ACID, S,S- DIOXIDE

Dissolve the product of Example 3 (0.85 gm) in methanol (2 mls) and cool to 0° C. under nitrogen. Add 1N sodium hydroxide (5 mls) portionwise. Refrigerate the mixture overnight. Acidify the resultant mixture with acetic acid, evaporate to dryness, and purify the residue by chromatography on a C-18 medium pressure reverse-phase column to yield the title compound of Example 4.

EXAMPLE 5

1-[[2-(S)-[5-[[6-CHLORO-3-CHLOROMETHYL-3,4-DIHYDRO-2H-1,2,4-BENZOTHIADIAZIN-7-YL]SULFONYLAMINO]-1-(S)-(ETHOXYCARBONYL)PENTYL]AMINO]-1-OXOPROPYL]-[2S-(2α,3aα,7aα)]-OCTAHYDRO-1H-INDOLE-2-CARBOXYLIC ACID, S,S-DIOXIDE

A. Combine N$^\epsilon$Cbz lysine, ethyl ester (30.0 g), t-butyl bromopropionate (44.78 g), triethylamine (14.8 ml) and DMF (120 ml) and stir under nitrogen at 75° C. until TLC shows no starting material present. Evaporate the solvent, dilute the resultant residue with water and extract with ethyl ether. Wash the organic layer with brine, dry over MgSO$_4$, filter and evaporate the solvent in vacuo.

Purify the resultant residue by column chromatography on 1,100 g silica gel (60–200 mesh), eluting with ether:hexane (50:50→75:50). Combine the desired fractions and evaporate the solvent in air. Further purify the resultant residue by HPLC using 2 Prep 500 cartridges and eluting with ether:hexane. Combine desired fractions, dry over MgSO$_4$ and evaporate the solvent in air to obtain a residue.

B. Combine 20% Pd(OH)$_2$/C (21.1 g) and anhydrous ethanol (25 ml) in a Parr shaker bottle, add the product of Part A (16.5 g) in ethanol (55 ml) and hydrogenate overnight under 60 p.s.i. H$_2$. Filter the resultant solution over filter paper and celite and evaporate the solvent to obtain a residue.

C. Dissolve the sulfonyl chloride prepared in Preparation 5 (2.4 g) in dry DME (15 ml). Add triethylamine (1 ml) and the product of Part B of this Example (2 g) in DMF (10 ml) and stir for 1 hour, or until TLC (silica, 10% MeOH in CH$_2$Cl$_2$) indicates no starting material is left. Add the resultant solution to ethyl acetate, wash with water, saturated NaHCO$_3$ and brine, dry over MgSO$_4$ and evaporate the solvent in vacuo. Purify the resultant residue on a Sephadex LH20 column to obtain a residue. FAB mass spec m/e=632 (M+H).

D. Treat the product of Part C in a manner similar to that described in Example 1, Part G.

E. Treat the product of Part D in a manner similar to that described in Example 1, Part H, first paragraph, substituting the camphorsulfonate salt of the benzyl ester of the octahydroindole (see Preparation 4 Part C) for the t-butyl ester.

Purify the resultant residue on a sephadex LH20 column, combine the desired fractions and evaporate the solvent. Dissolve the resultant residue in ethyl acetate, add dioxane saturated with HCl and evaporate the solvent to obtain the benzyl ester of the title compound. FAB mass spec m/e=817 (M+H).

F. Dissolve the product of Part E (600 mg) in acetic acid saturated with hydrogen bromide (6 ml). After 5 hours, evaporate the solvent and purify the resultant residue on a Sephadex LH20 column. Combine the desired fractions as determined by TLC (silica, MeOH:CH$_2$Cl$_2$:acetic acid, 10:90:4) and evaporate the solvent to obtain the title compound. FAB mass spec m/e=726 (M+H).

EXAMPLE 6

1-[[2-(S)-[1-(S)-CARBOXY-5-[[6-CHLORO-3-CHLOROMETHYL-3,4-DIHYDRO-2H-1,2,4-BENZOTHIADIAZIN-7-YL]SULFONYLAMINO]PENTYL]AMINO]-1-OXOPROPYL]-[2S-(2α,3aα,7aα)]-OCTAHYDRO-1H-INDOLE-2-CARBOXYLIC ACID, S,S-DIOXIDE

Add the product of Example 5, Part E (benzyl ester) to 1N aqueous NaOH (4 ml) and water (4 ml) and stir overnight. Add 1N HCl (4 ml) and ethanol. Charge the resultant solution to Dowex Ag 50 cation exchange resin by stirring batchwise for 20 minutes (60 ml resin, pre-washed with ethanol:water, 1:4). Prepare a column from the loaded resin, elute the column with ethanol:water (1:4) until the elute is pH 6, then elute with ethanol/water:pyridine (95:5). Combine the desired fractions as determined by TLC (silica, ethanol:water, 9:1). Further purify the resultant product on a Sephadex LH 20 column. Combine the desired fractions and evaporate the solvent to obtain the title compound. FAB mass spec m/e+698 (M+H).

EXAMPLE 7

N-[2-[[4-[[[6-CHLORO-3,4-DIHYDRO-3-(2-PHENYLETHYL)-2H-1,2,4-BENZOTHIADIAZIN-7-YL]SULFONYLAMINO]METHYL]PHENYL]-CARBONYL]AMINO-1-(S)-(ETHOXYCARBONYL)ETHYL]-(S)-ALANYL-(S)-PROLINE, S,S-DIOXIDE

A. Dissolve 4-cyanobenzoic acid, t-butyl ester (11.34 g) in ethanol (100 ml) saturated with anhydrous NH$_3$, add 5% Rh/Al$_2$O$_3$ (120 g) and hydrogenate in a Parr apparatus at 60 p.s.i. at room temperature for 2¾ hours. Filter the resultant solution through celite and evaporate the solvent to obtain a residue.

B. Dissolve the product of Part A (11.27 g) in dry THF (100 ml) add N,N,-diisopropylethyl amine (8.44 g) and cool to 0° C. in an ice bath. Add dropwise, slowly and with stirring, the sulfonyl chloride prepared in Preparation 2 (27.51 g) and let stand at 0° C. for 35 minutes. Remove the ice bath and stir at room temperature for 2½ hours or until TLC (silica, CH$_2$Cl$_2$:MeOH, 95:5) shows the reaction to be complete. Evaporate the solvent to obtain a residue.

C. Cool to 0° C. a solution of the product of Part B (3.00 g) in CH$_2$Cl$_2$ (25 ml) and add, slowly and with stirring, trifluoroacetic acid (25 ml). Stir for 30 minutes at 0° C., then at room tempeature for 2¼ hours or until TLC (as in Part B) shows the reaction to be complete. Evaporate the solvent to obtain a residue.

D. Dissolve triflate reagent as prepared in Preparation 1 (3.31 g) in CH$_2$Cl$_2$ (75 ml) and cool to 0° C.; add, slowly and with stirring a solution of PROTON SPONGE ® (4.24 g) and N-βCbz-2,3-diaminopropionate, ethyl ester (2.00 g) in CH$_2$Cl$_2$ (75 ml). Stir at 0° C. for 15 hours. Extract the solution with 10% citric acid (2x), then sat'd. NaHCO$_3$ (2x), dry the organic layer over MgSO$_4$, filter and evaporate the solvent. Purify the resultant residue by flash chromatography, eluting with CH$_2$Cl$_2$:EtOAc (88:12). Combine the desired fractions and evaporate the solvent. Dissolve the Cbz-diester (0.5 g) in ethanol (25 ml) containing 20% Pd(OH)$_2$C (0.15 g) and hydrogenate in a Parr apparatus at 50 p.s.i. at room temperature for 1 hour. Filter the resultant solution through celite and evaporate the filtrate in vacuo.

Combine the resultant residue (0.33 g) and the product of Part C (0.59 g) in dry DMF (7 ml), cool to 0° C. and add slowly 1-hydroxybenzotriazole (0.18 g) followed by N-methyl morpholine (0.13 g), then by DEC (0.25 g). Stir the mixture for 20 min. at 0° C., then at room temperature for 16 hours or until TLC (silica, ethanol:methanol, 85:15) indicates the reaction to be complete. Dilute the reaction mixture with CH$_2$Cl$_2$ and extract with saturated NaHCO$_3$, then with 10% aqueous citric acid. Dry the organic layer with MgSO$_4$, filter and evaporate the solvent in vacuo to obtain a residue.

E. Dissolve the product of Part D (0.75 g) in CH$_2$Cl$_2$ (5 ml) and cool to 0° C. Add, slowly and with stirring, trifluoroacetic acid (5 ml) and stir at 0° C. for 30 minutes, then at room temperature for 4 hours or until TLC (silica, CH$_2$Cl$_2$:MeOH, 90:10) indicates no starting material is left. Evaporate the solvent.

Purify the resultant residue by ion exchange chromatography on Biorad AG50-W-X2 resin (100–200 mesh, hydrogen form) previously equilibrated in ethanol:water. Elute with ethanol:water:pyridine, combine the desired fractions and evaporate the solvent to obtain a residue.

F. Treat the product of Part E in a manner similar to that described in Example 3, Parts F and G, substituting proline, t-butyl ester for the octahydro-1H-indole to obtain the title compound.

EXAMPLE 8

N-[5-[[6-CHLORO-3,4-DIHYDRO-3-(2-PHENYLETHYL)-2H-1,2,4-BENZOTHIADIAZIN-7-YL]SULFONYLAMINO]-1-(S)-(METHOXYCARBONYL)-PENTYN-3-YL]-(S)-ALANYL-(S)-PROLINE, S,S-DIOXIDE,HYDROCHLORIDE

A. Titrate a solution of diazomethane in ether into a solution of 1-amino-1-(S)-carboxy-5-(t-butoxycarbonyl amino)-3-pentyne (4 g) in ethanol (200 ml) until a yellow color remains. Evaporate the solvent to obtain 1-amino-1-(s)-methoxycarbonyl-5-(t-butoxycarbonylamino)-3-pentyne.

B. Add the product of Part A (4 g) and PROTON SPONGE ® (5 g) in dichloromethane (15 ml) dropwise to a stirred solution of triflate reagent (6.5 g) (See Preparation 1) in dichloromethane (10 ml) at −10° C. Stir the solution and slowly allow to warm to room temperature over 2 h. Filter the reaction mixture through celite, washing thoroughly with ethyl acetate. Wash the combined organic solution with 10% citric acid (3x), saturated sodium bicarbonate (2x) and brine (2x), dry over MgSO$_4$ and evaporate the solvent. Chromatograph on silica gel, eluting with ethyl acetate:hexane (1:4) containing 1% triethylamine to obtain 1-(S)-methoxycarbonyl-5-(t-butoxycarbonylamino)pentyn-3-yl-(S)-alanine, t-butyl ester.

C. Add the product of Part B (3.5 g) to a stirred solution of 4M HCL in dioxane (25 ml) at 0° and stir for 0.5 hours. Evaporate the solvent and triturate the residue with ether to obtain 1-(S)-methoxycarbonyl-5-amino-pentyn-3-yl-(S)-alanine, t-butyl ester, hydrochloride.

D. Add N-methylmorpholine (1.5 g) to a solution of the product of Part C (2.9 g) in tetrahydrofuran at 0°. Add 6-chloro-3,4-dihydro-2-(phenylethyl)-2H-1,2,4-benzothiadiazine-7-sulfonyl chloride, S, S-dioxide (3.9 g) (See Preparation 2) and stir the resulting mixture at room temperature overnight. Dilute the reaction mixture with ethyl acetate, wash with 0.5 N HCl (1x), saturated sodium bicarbonate (2x), and brine (1x), dry over MgSO4 and evaporate the solvent. Chromatograph on silica gel, eluting with ethyl acetate:dichloromethane to obtain a residue.

E. Add the product of Part D (4.8 g) to a 4M solution of HCL in dioxane (100 ml) and stir the resulting mixture at room temperature overnight. Evaporate the solvent then triturate the residue with ether to obtain a residue.

F. Treat the product of Part E in a manner similar to that described in Example 3, Part F, first paragraph, substituting (S)-proline, t-butyl ester for the octahydro-1H-indole, to obtain a residue.

Purify the resultant residue by chromatography on silica gel, eluting with ethyl acetate:CH2Cl2. Combine the desired fractions and evaporate the solvent to obtain a residue.

G. Treat the product of Part F in a manner similar to that described in Example 3, Part G to obtain the title compound.

EXAMPLE 9

N-[S-[[6-CHLORO-3,4,-DIHYDRO-3-(2-PHENYLETHYL)-2H1,2,4-BENZOTHIADIAZIN-7-YL]SULFONYLAMINO]-1-(S)-METHOXYCARBONYL)-(E)-PENTEN-3-YL]-(S)-ALANYL-(S)-PROLINE, S, S-DIOXIDE,HYDROCHLORIDE

A. Add a solution of 1-N-acetylamino-1-(S)-carboxy-5-(t-butoxycarbonylamino)-3-pentyne (5 g) in tetrahydrofuran (20 ml) dropwise to a stirred solution of sodium (1.2 g) in liquid ammonia (1.2 L). After 2 h, add ammonium hydroxide and water. Remove the ammonia, dissolve the residue in ethyl acetate, wash with 0.5N HCl (2x) and brine (3x), dry over MgSO4 and evaporate the solvent. Purify by precipitation from dichloromethane as the DCHA salt of (E)-1-N-acetylamino-1-carboxy-5-(t-butoxy-carbonylamino)-3-pentene.

B. Add cobalt chloride hexahydrate (50 mg) and Acylase I (aminoacylase from porcine kidney, grade 1, available from Sigma Chemical Co., St. Louis, MO) (100 mg) to a stirred solution of the product of Part A (3.5 g) in 0.1M, pH 7.5 phosphate buffer (120 ml) at 38°. After 16 hours, remove the protein with activated carbon and filter through celite. Adjust pH of the solution to 2.75 and remove the unreacted isomer by washing with ethyl acetate (3x). Adjust the pH to 6.5 and evaporate the solvent. Remove the salt from the residue by dissolving in ethanol (100 ml) and filtering through celite. Evaporate the solvent to obtain (E)-1-amino-1-(S)-carboxy-5-(t-butoxycarbonylamino)-3-pentene.

C. Substitute the product of Part B (i.e., the 3-pentene compound) for the 3-pentyne compound in the procedure of Example 8, Parts B to G to obtain the title compound.

EXAMPLE 10

1-[2-(S)-[[2-[4-[[[6-CHLORO-3-CHLOROMETHYL-3,4-DIHYDRO-2H-1,2,4-BENZOTHIADIAZIN-7-YL]SULFONYLAMINO]-METHYL]PHENYL-1-(S)-(ETHOXYCARBONYL)-PROPYL]AMINO]-1-OXOPROPYL]-(2S-(2α,3aα,-7aα)]-OCTAHYDRO-1-H-INDOLE-2-CARBOXYLIC ACID, T-BUTYL ESTER, S,S-DIOXIDE

A. To 1g of the compound of Example 3, part B, in THF, add HCl-saturated dioxane (30 ml). Stir the mixture at temperature for 5 hours under an inert atmosphere. Evaporate the solvent to obtain a dry foam as a hydrochloride salt.

B. Combine 3g of the product of Part A with 2.5g of octahydroindole-t-butyl ester (Preparation 3) in the manner described in Example 3, Part F to obtain 1-[2(S)-[[p-cyanophenyl-1(S)-(ethoxycarbonyl)propyl]amino]-1-oxopropyl]-[2S-(2α,3aα,7aα)]-octahydro-1H-indole-2carboxylic acid, t-butyl ester. FAB mass spec. M/e=501 (M+).

C. Hydrogenate 2.5g of the product of Part B in 150 ml of ethyl alcohol containing 5 ml of saturated HCl/dioxane at 55 psi in the presence of 500 mg of 10% Pd on C for 20 hours. Filter the resultant reaction mixture through celite to obtain 2.6g of amine.

D. Combine 850 mg of the product of Part C with 600 mg of 6-chloro-3-chloromethyl-3,4-dihydro-2H-1,2,4-benzothiadiazin-7-sulfonyl chloride, S,S-dioxide in 5ml of THF containing 0.8 ml of N-methylmorpholine and let stand overnight at room temperature. Dilute with EtOAC, wash with saturated NaCl, and evaporate the solvent. Purify the resultant residue by chromatography on Si02 with CH2Cl2/EtOAC as eluant to produce 700 mg of title compound. FAB mass spectrum shows M/e=844 (M+).

EXAMPLE 11

N-[N-[4-[4-[[[[6-CHLORO-3,4-DIHYDRO-3-[2-(2-PYRIDINYL)-ETHYL]-2H-1,2,4-BENZOTHIADIAZIN-7-YL]SULFONYL-AMINO]METHYL]PHENYL]-1-(S)-ETHOXYCARBONYL)-PROPYL]-(S)-ALANYL-(S)-PROLINE, T-BUTYL ESTER, S,S-DIOXIDE

A. To 6g of the amine of Example 3, Part C, in 25 ml of DME cooled with an ice-bath, add 1.9 ml of N-methylmorpholine. To this mixture add 5g of 4-amino-3-chloro-5-sulfonamidobenzenesulfonyl chloride in 25 ml of DME. Stir the reaction overnight with cooling under an inert atmosphere. Concentrate the resultant reaction mixture and partition the residue between EtOAc and H2O. Separate the organic layer and evaporate the solvent. Purify the resultant residue by chromatography on SiO2 using EtOAc/Hexanes as eluant to obtain 5g of an oil. FAB mass spectrum M/e=633 (M+).

B. Treat the product of Part A in a manner similar to that described in Example 10, Part A, to yield a dry foam. FAB mass spectrum M/e=614 (M+)

C. Combine 1.6 g of the product of Part B with 490 mg L-proline, t-butyl ester in the presence of 9 ml of DMF, 380 mg 1-hydroxybenzotriazole, 1.14 ml N-methylmorpholine and 550 mg DEC. Stir the reaction overnight, then extract and purify the resultant product as described in Example 3, Part F, using EtOAc/Hexanes as eluent to obtain a residue, FAB mass spectrum M/e=730 M+.

D. In 7 ml THF, combine the amino-sulphonamide obtained in Part C with 360 mg of (2-pyridinyl)propanal and 10 mg of p-toluenesulfonic acid and stir for 24 hours at room temperature in an inert atmosphere. Concentrate the reaction mixture and partition the resultant residue between EtOAc and water. Separate the organic phase, wash with dilute $NaHSO_3$, saturated $NaHCO_3$, saturated NaCl and dry with $MgSO_4$ Evaporate the solvent and chromatograph the residue on $SiO2$ using EtOAc as eluant to obtain 350 mg of the title compound. Mass spectrum, M/e=899 (M+).

EXAMPLE 12

1-[N-[2-[4-[[[6-CHLORO-3,4-DIHYDRO-3-(2-PHENYLETHYL)-2H-1,2,4-BENZOTHIADIAZIN-7-YL]SULFONYL]AMINOMETHYL]-THIAZOL-2-YLMETHYLTHIO]-1(S)-(METHOXYCARBONYL)ETHYL]-(S)-ALANYL]-CIS,SYN-OCTAHYDROINDOLE-2(S)-CARBOXYLIC ACID, S,S-DIOXIDE (A) Ethyl-4-Aminomethylthiazole-2-Carboxylate 1. Ethyl-thizaole-4-Carboxylate Combine ethylbromopyruvate (19.5 g, 100 mmole) in 50ml EtOH and thioformamide (4.27 g, 70 mmole) in 10 ml EtOH and stir at room temperature overnight. Pour into 1N HCl (100 ml) and extract with 190 ml diethyl ether. Separate the aqueous layer and treat with an excess of solid sodium bicarbonate. Extract the aqueous layer with diethylether (2 x 150 ml), dry over $MgSO_4$ and evaporate the solvent to obtain the title compound of Part A(1) as a syrup. Recrystallize from hexanes to obtain white needles, m.p. 52°–54° C.

2. 2-Carboamide-Thiazole

Treat 5.0 g of the product of Part A(1) with 100 ml of concentrated ammonium hydroxide solution overnight. Purge with $N_2$ for 2 hours and remove the solvent to obtain a crude product. Recrystallize using ethylacetate/pet ether to obtain the title compound, m.p. 122°–124° C.

3. 4-Cyano-Thiazole

Dissolve the product of Part A(2) (2.0 g, 14.50 mmoles) in 20 ml of dry $CH_2Cl_2$ and cool in an ice bath. Add trifluoroacetic anhydride (3.65 g, 16.50 mmoles) and stir at room temperature for 3 hours. Evaporate the solvent and recrystallize from ethylacetate/pet ether to obtain the title compound, m.p. 54°–56° C.

4. Ethyl-4-Cyanothiazole-2-Carboxylate

Cool diisopropyl amine (4.04 g, 40.0 mmoles) in dry THF in an ice bath under nitrogen Add n-butyl lithium (40 ml, 40 mmoles) and stir at 0° C. for 15 min. Cool the resultant reaction mixture to −78° C. and add a solution of the product of part A(3) (4.0 g, 36.36 mmoles) in 20 ml THF. Stir the reaction mixture at −78° C. for 30 minutes, add ethylchloroformate (3.93 g, 36.36 mmoles) and slowly warm the reaction mixture to room temperature. Add aqueous ammonium chloride and evaporate the solvent. Add $CH_2Cl_2$ (300 ml) to the resultant residue, wash with water, dry over $MgSO_4$ and evaporate the solvent to obtain the title compound. Purify the product by column chromatography using ethylacetate/pet ether.

5. Ethyl-4-Aminomethylthiazole-2-Carboxylate

Cool a disiamylborane (17.50 mmoles) solution in an ice bath under nitrogen. Add the product of Part A(4) (1.5 g, 8.24 mmoles) in 10 ml of dry THF and let stand at 0° C. for 2 days. Pour the reaction mixture into ice cold IN HCl and extract with diethyl ether. Separate the aqueous layer, treat with sodium bicarbonate, extract with 2×100 ml ethyl acetate, dry over $MgSO_4$ and evaporate the solvent to obtain the title compound. Use without further purification in Part B.

B. 1-N-[2-[4-[6-Chloro-3,4-Dihydro-3-(2-Phenylethyl)-2H-1,2,4,-Benzothiadiazin-7-yl]Sulfonyl]Aminomethyl]-2-Carboethoxythiazole, S,S-Dioxide Combine the product of Preparation 2 (1.2 mmoles) and the product of Part A (1.0 mmoles) in dry DMF (1.0 ml) and cool in an ice bath. Add dropwise triethyl amine (1.5 mmoles). Stir the resulting reaction mixture at room temperature for 16 hours. Evaporate the solvent under high vacuum, take up the residue in ethylacetate (100 ml), wash with water, dry over $MgSO_4$ and evaporate the solvent. Purify the resultant residue by column chromatography.

C. 1-[N-[2-[4-[6-Chloro-3,4-Dihydro-3-(2-Phenylethyl)-2H-1,2,4-Benzothiadiazin-7-yl]Sulfonyl]Aminomethyl]-2-Hydroxymethylthiazole, S,S-Dioxide Dissolve the product of Part B (1.0 mmole) in 25 ml dry THF and cool to −40° C. under nitrogen. Add $LiALH_4$ (1.5 mmole) and stir the resultant mixture at −40° C. for 1 hour. Add $Na_2SO_4 \cdot 10H_2O$, filter, dry over $MgSO_4$ and evaporate the solvent to obtain the title compound.

D. 1-[N-[2-[4-[6-Chloro-3,4-Dihydro-3-(2-Phenylethyl)-2H-1,2,4-Benzothiadiazin-7-yl]Sulfonyl]Aminomethyl]-2-Bromomethylthiazole, S,S-Dioxide Combine carbon tetrabromide (1.1 mmoles) and triphenyl phosphine (1.1 mmoles) in dry DMF (5 ml) at 0° C. under nitrogen and stir at 0° C. for ½ hour. Add a solution of the product of Part C (1.0 mmoles) in dry DMF (3 ml) and stir the reaction mixture at 0° C. for 1-2 hours. (Check progress of reaction by TLC). Pour the resultant mixture into ice cold water, extract with diethyl ether (2×150 ml), dry over $MgSO_4$ and evaporate the solvent. Purify the resultant residue by column chromatography.

E. Bis[[[1-(S)-(Methoxycarbonyl)-Ethyl]-(S)-Alanyl]-Cis,-Syn-Octahydroindole-2(S)-tert-Butoxycarbonyl]-disulphide 1. Cool a solution of L-cysteine (7.20 g, 0.027 moles) in 50 ml dry $CH_2Cl_2$ in an ice bath under $N_2$. Add N-methylmorpholine (16.8 g, 0.16 moles), then add a freshly prepared solution of triflate reagent (0.161 moles) (Preparation 1) in 200 ml $CH_2Cl_2$ dropwise over 2 hours. Stir the resulting reaction mixture overnight at room temperature. Wash the reaction mixture with 2×100 ml of water, then 2 x 100 ml of brine, dry over $MgSO4$, and evaporate the solvent. Column chromatograph the resultant residue using 40% ethyl acetate:60% pet ether to obtain a syrup.

2. Cool a solution of the product of Part E(1) in 50 ml dioxane in an ice bath. Add 150 ml of a solution of saturated dioxane:HCl and stir at room temperature for 3 hours. Reduce the volume of the reaction mixture to 50 ml and add 150 ml of ethyl acetate to precipitate the product as the hydrochloride salt.

3. Cool a solution of the product of Part E(2) (1.0 mmole) in 10 ml dry DMF in an ice bath. Add 1-hydroxybenzotriazole hydrate (2.2 mmoles), 1-(dimethylaminopropyl)-3-ethyl-carbodiimide (3.0 mmole) and 2-carboxy-perhydroindole t-butyl ester (2.3 mmole) (Preparation 3) and stir the resulting solution at 0° C. Add triethylamine dropwise (6.0 mmoles) and stir the resulting reaction mixture over-night at room temperature. Evaporate the solvent, dissolve the residue in 200 ml of ethylacetate, wash with water, brine, and dry over MgSO$_4$ Evaporate the solvent and column chromatograph the resultant residue using 60% ethylacetate:40% pet ether.

F. Cool 5 ml of dry methanol in an ice bath under nitrogen, add sodium borohydride (10.0 mmole) and stir at 0° C. for 10 minutes. Add the product of Part E (0.60 mmoles) in 5 ml dry methanol and stir the resulting mixture for 5 minutes at 0° C. Add the product of Part D (1.2 mmoles) in 5 ml THF, warm the mixture to room temperature and stir at room temperature for 2 hours. Evaporate the solvent and take up the resultant residue in ethylacetate. Extract with 10% citric acid, NaHCO$_3$ solution and brine, dry over MgSO$_4$ and evaporate the solvent. Chromatograph the residue to obtain the t-butyl ester of the title compound of Example 12.

G. Treat the product of Part F in a manner similar to that described in Example 3, Part G, to obtain the title compound. Mass spectrum m/e=925 (M+).

EXAMPLE 13

1-[2(S)-[[4-[4-[[[6-CHLORO-3,4-DIHYDRO-3-(1-IMIDAZOLYLMETHYL)-2H-1,2,4-BENZOTHIADIAZIN-7YL-SULFONYLAMINO]METHYL]PHENYL]-1(S)-(ETHOXYCARBONYL)-BUTYL]AMINO]-1-OXOPROPYL]-CIS,SYN-OCTAHYDROINDOLE-2(S)-CARBOXYLIC ACID, DIHYDROCHLORIDE

A. Substituting 2-(4-cyano)phenylpropyl bromide for 2-(4-cyano)phenylethyl bromide, carry out the procedure described in Example 3, Parts A–C to obtain the hydrochloride salt.

B. Treat the product of Part A as described in Example 11, Parts A and B, to obtain a residue C. Combine the product of Part B and perhydroindole-2carboxlic acid, t-butyl ester (Preparation 3) as described in Example 11, part C and stir overnight. Evaporate the solvent and partition the resultant residue between 5% NaHCO$_3$ and EtOAc. Separate the EtOAc layer, dry over MgSO$_4$ and evaporate the solvent. Chromatograpth the resultant residue by flash chromatograpthy on SiO$_2$ (150 gm) eluting with 60% EtOAc: 40% hexane. Combine the desired fractions and evaporate the solvent to obtain a residue.

D. Dissolve sodium spheres (2.3g) indry methanol (100 ml) at room temperature, add imidazole (6.3 ml) and stir for 1 hour at room temperature. Add bromoacetaldehyde dimethylacetal (11.8 ml) and heat the resultant mixture overnight at reflux. Evaporate the solvent in vacuo, partition the resultant residue between EtOAc and water, dry the organic layer over MgSO$_4$, and evaporate the solvent. Purify the resultant residue by flash chromatography on SiO$_2$ (250 g), eluting with 4% CH$_3$OH in CH$_2$Cl$_2$. Combine the desired fractions and evaporate the solvent to obtain (1-imidazolyl)acetaldehyde dimethylacetal.

E. Combine the products of Part C (0.50g) and Part D (0.13g) in THF (20 ml), add HCl-saturated dioxane and stir, following the reaction by thin layer chromatography on silica gel (elute with 5% CH$_3$OH in CH$_2$Cl$_2$) and adding HCl-dioxane until the reaction is complete. Evaporate the solvent, partition the resultant residue between 5% NaHCO$_3$ and EtOAc, wash the organic layer with brine, dry over MgSO$_4$, and evaporate the solvent to obtain a residue. Purify the resultant residue by flash chromatography on SiO$_2$ (25 g), eluting with 3% CH$_3$OH in CH$_2$Cl$_2$. Combine the desired fractions and evaporate the solvent to obtain the t-butyl ester of the title compound.

F. Stir the product of Part E in HCl-saturated dioxane (200 ml) at room temperature and under nitrogen for 6 hours. Evaporate the solvent in vacuo at room temperature to obtain the title compound, M/e=834 (M+).

In a similar manner, using appropriate starting materials and reagents, the following compounds may be prepared:

1-[2-(S)-[[1-(S)-carboxy-2-[4-[[[6-chloro-3-(cyclopentylmethyl)-3,4-dihydro-2H-1,2,4-benzothiadiazin-7-yl]sulfonylamino]methyl]phenylmethoxy]ethyl]amino]-1-oxopropyl]-[2S-(2α, 3aα, 7aα)]-octahydro-1H-indole-2-carboxylic acid, S,S-dioxide 1-[2-(S)-[[1-(S)-carboxy-2-[4-[[[6-chloro-3-(dichloromethyl)-3,4-dihydro-2H-1,2,4-benzothiadiazin-7-yl]sulfonylamino]methyl]phenylmethoxy]ethyl]amino]-1-oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1-oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3-(cyclopentylmethyl)-3,4-dihydro-2H-1,2,4-benzothiadiazin-7-yl]sulfonylamino]methyl]phenyl]propyl]amino]-1-oxopropyl]-[2S-(2α, 3aα, 7aα)]-octahydro-1H-indole-2-carboxylic acid, S,S-dioxide 1-[2-(S)-[[1-(S)-carboxy-3-[4-[[[6-chloro-3-(dichloromethyl)-3,4-dihydro-2H-1,2,4-benzothiadiazin-7-yl]sulfonylamino]methyl]phenyl]propyl]amino]-1-oxopropyl]-[2S-(2α, 3aα, 7aα)]-octahydro-1H-indole-2-carboxylic acid, S,S-dioxide 1-[2-(S)-[[1-(S)-carboxy-2-[4-[[[6-chloro-3,4-dihydro-3-(2-phenylethyl)-2H-1,2,4-benzothiadiazin-7-yl]sulfonylamino]methyl]phenyl]ethyl]amino]-1-oxopropyl]-[2S-(2α, 3aα, 7aα)]-octahydro-1H-indole-2-carboxylic acid, S,S-dioxide N-[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]-(S)-alanyl-(S)-proline, S,S-dioxide N-[1-(S)-carboxy-3-[4-[[[6-chloro-3-(cyclopentylmethyl)-3,4-dihydro-2H-1,2,4-benzothiadiazin-7-yl]sulfonylamino]methyl]phenyl]propyl]-(S)-alanyl-(S)-proline, S,S-dioxide N-[1-(S)-carboxy-3-[4-[[[6-chloro-3-(dichloromethyl)-3,4-dihydro-2H-1,2,4-benzothiadiazin-7-yl]sulfonylamino]methyl]phenyl]propyl]-(S)-alanyl-(S)-proline, S,S-dioxide N-[1-(S)-carboxy-2-[4-[[[6-chloro-3,4-dihydro-3-(2-phenylethyl)-2H-1,2,4-benzothiadiazin-7-yl]sulfonylamino]methyl]phenyl]ethyl]-(S)-alanyl-(S)-proline, S,S-dioxide N-[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]-(S)-alanyl-(S)-(4-cyclohexyl)proline, S,S-dioxide 7-N-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1-oxopropyl]-1,4-dithia-7-azaspiro[4.4]nonane-8-(S)-carboxylic acid, S,S-dioxide 1-[2-(S)-[[1-(S)-carboxy-3-[4-[[[6-chloro-3,4-dihydro-3-(2-phenylethyl)-2H-1,2,4-benzothiadiazin-7-yl]sulfonylamino]methyl]phenyl]propyl]amino]-1-oxopropyl]-1H-2,3-dihydroindole-2-(S)-carboxylic acid S,S-dioxide 1-[2-(S)-[[2-[4-[[[6-chloro-3,4-dihydro-3-(2-phenylethyl)-2H-1,2,4-benzothiadiazin-7-yl]sulfonylamino]methyl]phenylmethoxy]-1-(S)-[(2,2-dimethyl-1,3-dioxolan-4-yl)methoxycarboxyl]ethyl]amino]-1-oxopropyl]-[2S-(2α, 3aα, 7aα)]-octahydro-1H-indole-2-carboxylic acid, S,S-dioxide 1-[2-(S)-[[3-[4-[[[6-chloro-3,4-dihydro-3-(2-phenylethyl)-2H-1,2,4-benzothiadiazin-7-yl]sulfonylamino]methyl]phenyl]-1-(S)-[(2,2-dimethyl-1,3-dioxolan-4-yl)methoxycarbonyl]propyl]amino]-1-oxopropyl]-[2S-(2α, 3aα, 7aα)]-octahydro-1H-indole-2-carboxylic acid, S,S-dioxide 1-[2-(S)-[[3-[4-[[[6-chloro-3,4-dihydro-3-(2-phenylethyl)-2H-1,2,4-benzothiadiazin-7-yl]sulfonylamino]methyl]phenyl]-1-(S)-(ethoxycarbonyl)propyl]amino]-1-oxopropyl]-[2S-(2α, 3aα, 7aα)]-octahydro-1H-indole-2-carboxylic acid, S,S-dioxide N-[3-[4-[[[6-chloro-3,4-dihydro-3-(2-phenylethyl)-2H-1,2,4-benzothiadiazin-7-yl]sulfonylamino]methyl]phenyl]-1-(S)-(ethoxycarbonyl)propyl]-(S)-alanyl-(S)-proline, S,S-dioxide.

N-[3-[4-[[[6-chloro-3,4-dihydro-3-(2-phenylethyl)-2H-1,2,4-benzothiadiazin-7-yl]sulfonylamino]methyl]phenyl]-1-(S)-[(2phenoxy)ethoxycarbonyl)propyl]-(S)-alanyl-(S)-proline, S,S-dioxide.

N-[3-[4-[[[6-chloro-3,4-dihydro-3-(2-phenylethyl)-2H-1,2,4-benzothiadiazin-7-yl]sulfonylamino]methyl]phenyl]-1-(S)-[(2,3dihydroxy)propoxycarbonyl]propyl]-(S)-alanyl-(S)-proline, S,S-dioxide.

N-[3-[4-[[[6-chloro-3-(cyclopentylmethyl)-3,4-dihydro-2H-1,2,4-benzothiadiazin-7-yl]sulfonylamino]methyl]phenyl]-1-(S)-(ethoxycarbonyl)propyl]-(S)-alanyl-(S)-proline, S,S-dioxide N-[3-[4-[[[6-chloro-3,4-dihydro-3-(2-phenylethyl)-2H-1,2,4-benzothiadiazin-7-yl]sulfonylamino]methyl]phenyl]-1-(S)-[(2,2-dimethyl-1,3-dioxolan-4-yl)methoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2,2-dimethyl-1,3-dioxolan-4-yl)methoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2-phenoxy)ethoxycarbonyl]propyl]-(S)-alanyl-(S)-proline, S,S-dioxide N-[3-[4-[[[6-chloro-3-(cyclopentylmethyl)-3,4-dihydro-2H-1,2,4-benzothiadiazin-7-yl]sulfonylamino]methyl]phenyl]-1-(S)-[(2,3-dihydroxy)propoxycarbonyl]propyl]-(S)-alanyl-(S)-proline, S,S-dioxide 1-[2-[[2-[[4-[[[4-chloro-3-[[(phenylmethyl)amino]sulfonyl]phenyl]sulfonylamino]methyl]phenyl]methoxy]-1-(S)-(ethoxycarbonyl)ethyl]amino]-1-oxopropyl]-[2S-(2α,3aα,7aα)]-octahydro-1H-indole-2-carboxylic acid 1-[2-[[2-[[4-[[[4-chloro-3-[[(phenylmethyl)amino]sulfonyl]phenyl]sulfonylamino]methyl]phenyl]methoxy]-1-(S)-(carboxy)ethyl]amino]-1-oxopropyl]-[2S-(2α, 3aα,7aα)]-octahydro-1H-indole-2-carboxylic acid N-[2-[[4-[[[4-chloro-3-[[(phenylmethyl)amino]sulfonyl]phenyl]sulfonylamino]methyl]phenyl]methoxy]-1-(S)-(ethoxycarbonyl)ethyl]-(S)-alanyl-(S)-proline N-[2-[[4-[[[4-chloro-3-[[(phenylmethyl)amino]sulfonyl]-phenyl]sulfonylamino]methyl]phenyl]methoxy]-1-(S)-(carboxy)ethyl]-(S)-alanyl-(S)-proline 1-[2-[[2-[[4-[[[3-(amino)sulfonyl-4chlorophenyl]sulfonylamino]methyl]phenyl]methoxy]-1-(S)-(ethoxycarbonyl)ethyl]amino]-1-oxopropyl]-[2-S-(2α,3aα,7aα)]-octahydro-1H-indole-2-carboxylic acid 1-[2-[[2-[[4-[[[3-(amino)sulfonyl-4chlorophenyl]sulfonylamino]methyl]phenyl]methoxy]-1-(S)-(carboxy)ethyl]amino]-1-oxopropyl]-[2S-(2α, 3aα,7aα)]-octahydro-1H-indole-2-carboxylic acid N-[2-[[4-[[[3-(amino)sulfonyl-4-chlorophenyl]sulfonylamino]methyl]phenyl]methoxy]-1-(S)-(ethoxycarbonyl)ethyl]-(S)-alanyl-(S)-proline N-[2-[[4-[[[3-(amino)sulfonyl-4-chlorophenyl]sulfonylamino]methyl]phenyl]methoxy]-1-(S)-(ethoxycarbonyl)ethyl]-(S)-lysyl-(S)-proline N-[2-[[4-[[[3-(amino)sulfonyl-4-chlorophenyl]sulfonylamino]methyl]phenyl]methoxy]-1-(S)-(carboxy)ethyl]-(S)-alanyl-(S)-proline N-[2-[[4-[[[3-(amino)sulfonyl-4-chlorophenyl]sulfonylamino]methyl]phenyl]methoxy]-1-(S)-(carboxy)ethyl]-(S)-lysyl-(S)-proline N-[2-[[4-[[[3-(amino)sulfonyl-4-chlorophenyl]sulfonylamino]methyl]phenyl]methoxy]-1-(S)-[(2,2-dimethyl-1-oxopropoxy)methoxycarbonyl]ethyl]-(S)-alanyl-(S)-proline N-[3-[4-[[[6-chloro-3,4-dihydro-2H-1,2,4-benzothiadiazin-7-yl]sulfonylamino]methyl]phenyl]-1-(S)-(ethoxycarbonyl)propyl]-(S)-alanyl-(S)-proline, S, S-dioxide N-[3-[4-[[[6-chloro-3,4-dihydro-2H-1,2,4-benzothiadiazin-7-yl]sulfonylamino]methyl]phenyl]-1-(S)-[2,2-dimethyl-1-oxopropoxy)methoxycarbonyl]propyl]-(S)-alanyl-(S)-proline, S S-dioxide N-[3-[4-[[[6-chloro-3,4-dihydro-2H-1,2,4-benzothiadiazin-7-yl]sulfonylamino]methyl]phenyl]-1-(S)-(ethoxycarbonyl)propyl]-(S)-lysyl-(S)-proline, S, S-dioxide N-[1-(S)-carboxy-3-[4-[[[6-chloro-3,4-dihydro-2H-1,2,4-benzothiadiazin-7-yl]sulfonylamino]methyl]phenyl]propyl]-(S)-alanyl-(S)-proline, S, S-dioxide N-[1-(S)-carboxy-3-[4-[[[6-chloro-3,4-dihydro-2H-1,2,4-benzothiadiazin-7-yl]sulfonylamino]methyl]phenyl]propyl]-(S)-lysyl-(S)-proline, S, S-dioxide N-[1-(S)-carboxy-3-[4-[[[6-chloro-3-chloromethyl-3,4-dihydro-2H-1,2,4-benzothiadiazin-7-yl]sulfonylamino]methyl]phenyl]propyl]-(S)-alanyl-(S)-proline, S, S-dioxide N-[1-(S)-carboxy-3-[4-[[[6-chloro-3-chloromethyl-3,4-dihydro-2H-1,2,4-benzothiadiazin-7-yl]sulfonylamino]methyl]phenyl]propyl]-(S)-lysyl-(S-)proline, S, S-dioxide N-[3-[4-[[[6-chloro-3-chloromethyl-3,4-dihydro-2H-1,2,4-benzothiadiazin-7-yl]sulfonylamino]methyl]- phenyl]-1-(S)-[2,2-dimethyl-1-oxopropoxy)methoxycarbonyl]propyl]-(S)-alanyl-(S)-proline, S̲, S̲-dioxide N-[3-[4-[[[6-chloro-3-chloromethyl-3,4̲-dihydro-2H̲-1,2,4-benzothiadiazin-7-yl]sulfonylamino]methyl]phenyl]-1-(S)-(ethoxycarbonyl)propyl]-(S)-alanyl-(S)-proline, S̲, S̲-dioxide 1-[2-(S̲)-[[2-[4-[[[6-chloro-3-chloromethyl-3,4-dihydro-2H̲-1,2,4-benzothiadiazin-7-yl]sulfonylamino]methyl]p̲henylmethoxy]-1-(S)-(ethoxycarbonyl)ethyl]amino]-1-oxopropyl]-[2S-(2α, 3aα,7aα)]-octahydro-1H̲-indole-2-carboxylic acid, S̲, S̲-dioxide 1-[2-(S)-[[1-(S)-carboxy-2-[4̲-[[[6-chloro-3-chloromethyl-3,4-dihydro-2H̲-1,2,4-benzothiadiazin-7-yl]sulfonylamino]methyl]p̲henyl]ethyl]amino]-1-oxopropyl]-[2S-(2α,3aα,7aα)]-octahydro-1H̲-indole-2-carboxylic acid, S̲, S̲-dioxide 1-[2̲-(S̲)-[[1-(S)-carboxy-2-[4-[[[6-chloro-3-chloromethyl-3,4-dihydro-2H̲-1,2,4-benzothiadiazin-7-yl]sulfonylamino]methyl̲]phenylmethoxy]ethyl]amino]-1-oxopropyl]-[2S-(2α,3aα,7aα)-octahydro-1H̲-indole-2-carboxylic acid, S̲, S̲-dioxide 1-[2-(S)-[[1-(S̲)-c̲arboxy-2-[4-[[[6-chloro-3,4-dihydro-2H̲-1,2,4-benzothiadiazin-7yl]sulfonylamino]methyl]p̲henylmethoxy]ethyl]amino]-1-oxopropyl]-[2S-(2α,3aα,7aα)]-octahydro-1H̲-indole-2-carbóxylic acid, S̲, S̲-dioxide N-[1-(S)-carboxy-5-[6-chloro-3,4-dihydro-2H̲-1,2,4-benzothiadiazin-7-yl]sulfonylamino]pentyn-3-y̲l]-(S)-alanyl-(S)-proline, S̲, S̲-dioxide N-[5-[6-chloro-3,4̲-dihydro-2H̲-1,2,4-benzothiadiazin-7-yl]-sulfonylamino]-1-(S)-(ethoxycarbonyl)pentyn-3-yl]-(S)-alanyl-(S)-proline, S̲, S̲-dioxide 1-[4-carboxy-5-[4-[[[6-chloro-3̲-(cyclopentylmethyl)-3,4-dihydro-2H̲-1,2,4-benzothiadiazin-7-yl]sulfonylamino]methyl]phenylmethoxy]-1-oxopentyl]-octahydro-1H̲-indole-2-carboxylic acid, S̲, S̲-dioxide N-[2-(S)-[1̲-(S)-carboxy-3-[4-[[[6-chloro-3̲,4-dihydro-3-(2-phenylethyl)-2H̲-1,2,4-benzothiadiazin-7-yl]sulfonyl-amino]methyl]p̲henyl]propoxy]-1-oxopropyl]-(S)-proline, S̲, S̲-dioxide N-[N-[3̲-[5-[[[[6-chloro-3,4-dihydro-3-(2-phenylethyl)-2H̲-1,2,4-benzothiadiazin-7-yl]sulfonyl]amino]methyl]-1H̲-imidazol-2-yl]-1-(ethoxycarbonyl)propyl]-(S̲)-alanyl-(S̲)-proline, S̲,S̲-dioxide N-[N-[3-[5-[[[[6-chl̲oro-3,4-dihydro-3-(2-phenylethyl)-2H̲-1,2,4-benzothiadiazin-7-yl]sulfonyl]amino]methyl]-2-thiazolyl]-1-(ethoxycarbonyl)propyl]-(S)-alanyl-(S)-proline, S̲,S̲-dioxide The compounds of this invention are useful in view of their pharmacological properties. In particular, they possess activity as antihypertensive agents, as evidenced b their ability to reduce blood pressure in mammals in which the blood pressure has become abnormally elevated. For example, compounds of this invention lower blood pressure in the spontaneously hypertensive rat (SHR) model. Compounds of this invention also show activity as diuretic agents.

Since these compounds are also believed to act as angiotensin converting enzyme inhibitors, it is contemplated that they may be used in treating other cardiovascular disorders, for example congestive heart failure, in the same manner as other ACE inhibitors such as captopril and enalapril may be used. In addition, compounds of this invention may be used in the treatment of glaucoma by topical application.

The compounds of this invention can be combined with pharmaceutical carriers and administered in a variety of well-known pharmaceutical forms suitable for oral or parenteral administration to provide compositions useful in the treatment of cardiovascular disorders and particularly mammalian hypertension.

The daily antihypertensive dose of the compounds of this invention will be typically in the range of about 1 to about 25 mg/kg, of mammalian weight, administered in single or divided doses. The exact dose to be administered is determined by the attending clinician and is dependentuupon the potency of the administered compound, i.e. where the particular compound lies within the above range, as well as upon the age, weight and condition of the individual.

Generally, in treating humans having hypertension, the compounds of this invention may be administered to patients in need of such treatment in dosage range of about 5 to about 500 mg per patient generally given several times a day, thus giving a total daily dose of from about 5 to about 2000 mg per day.

The antihypertensive compositions containing the compounds of this invention will preferably contain from about 5 to about 250 mg of the active compound per dosage unit.

The compositions of the present invention are most preferably administered orally. Typical formulations for oral administration are those such as tablets, capsules, syrups, elixirs or suspensions. Typical injectable formulations include solutions and suspensions. Also contemplated are mechanical delivery systems, e.g. transdermal dosage forms.

The typical acceptable pharmaceutical carriers for use in the formulations described above are exemplified by: sugars such as lactose, sucrose, mannitol and sorbitol; starches such a corn starch tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

In the following examples the "active ingredient" is 1-[N-[3-[4-[[[6-chloro-3,4-dihydro-3-(2-pyridylethyl)-2H̲-1,2,4-benzothiadiazin-7-yl)sulfonylamino]methyl]phenyl]-1(S)-ethoxycarbonyl)propyl]-(S)-alanyl)-cis,-syn-octahydroindole-2(S)-carboxylic acid, S,S-dioxide. It is contemplated, however, that this compound may be replaced by equally effective quantities of other compounds within the scope of formula I.

EXAMPLE 14

| Capsule | Amount (mg) | |
| --- | --- | --- |
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.00 | 500.00 |

Blend the active ingredient, lactose, and corn starch until uniform; then blend the magnesium stearate into the resulting powder. Encapsulate the mixture into suitably sized two-piece hard gelatin capsules.

EXAMPLE 15

| Tablet | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120. ml (evaporates) | 60. ml (evaporates) |
| Corn Starch | 75.0 | 37.5 |
| Magnesium Stearate | 2.0 | 1.0 |
| | 500.00 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintergration.

EXAMPLE 16

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°-70° C. and cool the solution to 25°-25° C. Charge and dissolve all other excipients and the active ingredient. Bring the solution to final volume, filter it through a sterilizing membrane and fill into sterile containers.

Similarly, substitute other compounds of the present invention to prepare other compositions of the present invention.

We claim:

1. A compound represented by the formula

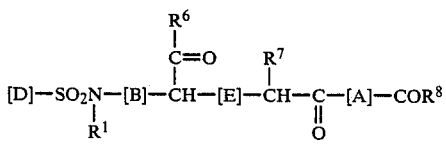

and the pharmaceutically acceptable salts thereof, wherein:

A is

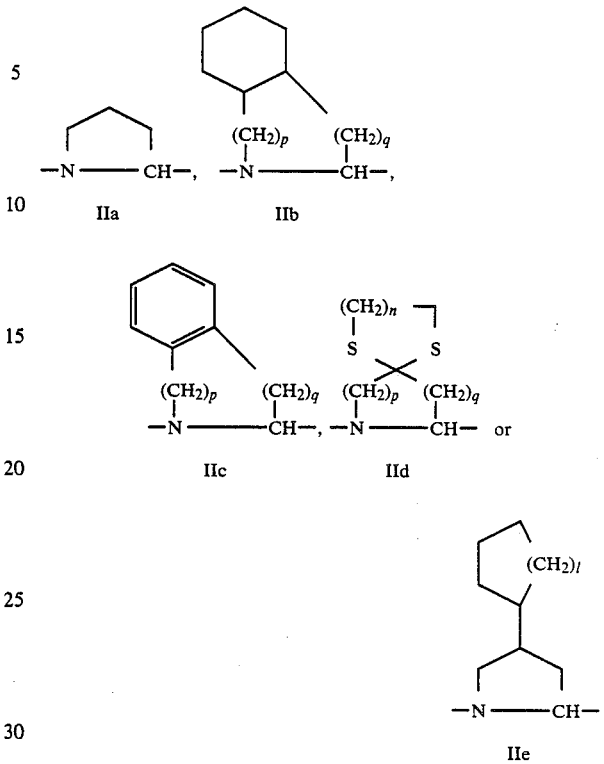

l is 1 or 2;
n is 0 or 1;
p and q are 0, 1 or 2, provided that in structurces IIb and IIc the sum of p and q is 1 or 2, and that in formula IId, p is not 0;
B is —[J]—[L]—[M]—;
D is

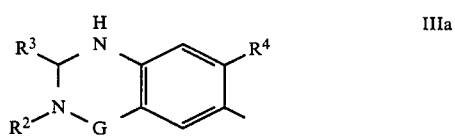

E is —NH—, —O—, —S—, or —CH$_2$—;
G is —SO$_2$—;
J is —(CH$_2$)$_s$— or —((CH$_2$)$_r$—W)—;
L is a chemical bond, cis- or trans-lower alkene, lower alkyne, -Z-aryl-, -aryl-Z-, -Z-cycloalkyl-, or -cycloalyl-Z-, wherein aryl is

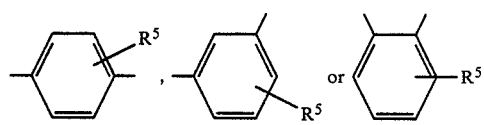

and cycloalkyl is

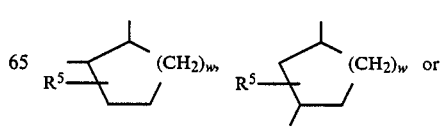

-continued

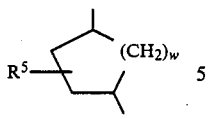

wherein
w is 1, 2 or 3;
M is —(CH$_2$)$_u$— or —((CH$_2$)$_t$—X—(CH$_2$)$_v$)—;
W is

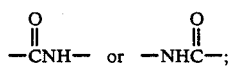

X and Z are independently a chemical bond,

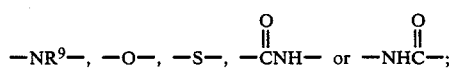

s, u and v are independently 0–5;
t is 1–5;
R$^1$, R$^2$ and R$^9$ are independently hydrogen, lower alkyl or lower acyl;
R$^3$ is 2-, 3- or 4-pyridylloweralkyl, 2-, 4- or 5-thiazolylloweralkyl, 2-, 4- or 5-1H-imidazolylloweralkyl, 1-imidazolylloweralkyl, 1-morpholinoloweralkyl or hydroxyphenylloweralkyl;
R$^4$ is chlorine or CF$_3$;
R$^5$ is hydrogen, halogen, lower alkyl, lower acyl, lower alkoxy, haloloweralkyl or phenylloweralkyl;
R$^7$ is hydrogen, lower alkyl or aminoloweralkyl;
R$^6$ and R$^8$ are independently hydroxy, alkoxy having from 1 to 8 carbon atoms, benzyl, allyl, R$^{10}$—Q—$_r$—(CH$_2$)$_m$—O—, wherein Q is oxygen or sulfur, r is 0 or 1 and m is 2 to 4,

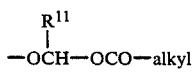

wherein the alkyl has from 3 to 8 carbon atoms,

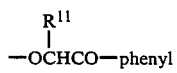

wherein the phenyl may be substituted with group T defined below, 1-glyceryl,

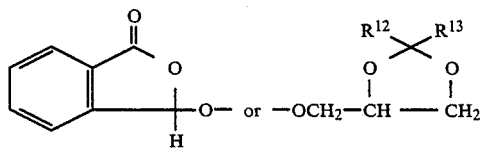

R$^{10}$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;

R$^{11}$ is hydrogen or alkyl having from 1 to 8 carbon atoms;
R$^{12}$ is hydrogen, lower alkyl, unsubstituted or substituted phenyl and substituted or unsubstituted phenyl lower alkyl, wherein phenyl may be substituted by group T;
R$^{13}$ is hydrogen or lower alkyl; and
provided that if L is alkene or alkyne, J is —(CH$_2$)$_s$— wherein is 1–5; provided that if L is —Z—aryl— or —Z—cycloalkyl—, J is —(CH$_2$)$_s$— wherein s is 2–5; provided that if L is alkene, alkyne, —aryl—Z— or —cycloalkyl—Z—, M is —(CH$_2$)$_u$— wherein u is 1–5; provided that if s and u are each zero, L is aryl or cycloalkyl (i.e. Z is a bond); and provided that if s and v are each zero, L is aryl or cycloakyl (i.e. Z is a bond).

2. A compound of claim 1, wherein A is represented by formula IIa or IIb wherein p is 0 and q is 1.
3. A compound of claim 1, wherein E is —NH—.
4. A compound of claim 1 wherein R$^7$ is hydrogen, methyl or aminobutyl.
5. A compound of claim 1 wherein R$^3$ is 2-pyridylethyl.
6. A compound of claim 1 wherein R$^6$ and R$^8$ are independently hydroxy, methoxy, ethoxy, phenoxyethoxy, pivaloyloxymethoxy, 1-glyceryl or

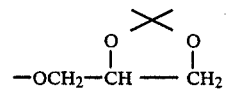

7. A compound of claim 1 wherein B is of the formula

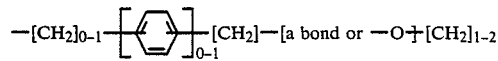

i.e., where J is —(CH$_2$)$_s$— and s is 0–1, L is a bond or —Z—aryl— wherein Z is a bond, and M is —((CH$_2$)$_t$—X—(CH$_2$)$_v$), wherein t is 1, v is 1–2, and X is a bond or —O—.
8. A compound of claim 7 which is 1-[N-[3-[4-[[[6-chloro-3,4-dihydro-3-(2-pyridylethyl)-2H-1,2,4-benzothiadiazin-7-yl)sulfonylamino]methyl]phenyl]-1(S)-(ethoxycarbonyl)-propyl]-(S)-alanyl]-cis, syn-octahydroindole-2(S)-carboxylic acid, S,S-dioxide.
9. An antihypertensive pharmaceutical composition comprising an anthihypertensive effective amount of compound of claim 1 together with a pharmaceutically acceptable carrier therefor.
10. A method for reducing blood pressure in hypertensive mammals which comprises administering to a hypertensive mammal a composition comprising an antihypertensive effective amount of a compound of claim 1 together with a pharmaceutically acceptable carrier therefor.
11. A compound represented by the formula

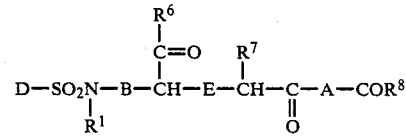

and the pharmaceutically acceptable salts thereof, wherein:

A is l is 1 or 2;
n is 0 or 1;
p and q are 0, 1 or 2, provided that in structures IIb and IIc the sum of p and q is 1 or 2, and that in formula IId, p is not 0;
B is —J—L—M—;
D is E is —NH—, —O—, —S—, or —CH$_2$—;
G is —SO$_2$—;
J is —(CH$_2$)$_s$— or —((CH$_2$)$_t$—W)—;
L is a 5- or 6-membered heterocyclic radical comprising 3 to 5 carbon atoms and 1 or 2 heteroatoms selected from N, O and S, or a R$^5$-substituted heterocycyclic radical
M is —(CH$_2$)$_u$— or —((CH$_2$)$_t$—X—(CH$_2$)$_v$)—;
W is $$-\overset{O}{\underset{\|}{C}}NH- \text{ or } -NH\overset{O}{\underset{\|}{C}}-;$$

X and Z are independently a chemical bond,

—NR$^9$—, —O—, —S—, —$\overset{O}{\underset{\|}{C}}$NH— or —NH$\overset{O}{\underset{\|}{C}}$—;

s, u and v are independently 0–5;
t is 1–5;
R$^1$, R$^2$ and R$^9$ are independently hydrogen, lower alkyl or lower acyl;
R$^3$ is hydrogen, lower alkyl, haloloweralkyl, phenylloweralkyl, (cycloalkyl)loweralkyl, aminomethyl, loweralkylaminomethyl, phenyl(lower)alkylaminomethyl, (cycloalkyl)loweralkylthiomethyl, loweralkylthiomethyl or haloloweralkylthiomethyl;
R$^4$ is chlorine or CF$_3$;
R$^5$ is hydrogen, halogen, lower alkyl, lower acyl, lower alkxoy, haloloweralkyl or phenylloweralkyl;
R$^7$ is hydrogen, lower alkyl or aminoloweralkyl;
R$^6$ and R$^8$ are independently hydroxy, alkoxy having form 1 to 8 carbon atoms, benzyl, allkyl, R$^{10}$—Q—$_r$—(CH$_2$)$_m$—O—, wherein Q is oxygen or sulfur, r is 0 or 1 and m is 2 to 4, $$-O\overset{R^{11}}{\underset{|}{C}}H-OCO-\text{alkyl}$$

wherein the alkyl has from 3 to 8 carbon atoms, $$-O\overset{R^{11}}{\underset{|}{C}}HCO-\text{phenyl}$$

wherein the phenyl may be substituted with group T defined below, 1-glyceryl,

R$^{10}$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
R$^{11}$ is hydrogen or alkyl having from 1 to 8 carbon atoms;
R$^2$ is hydrogen, lower alkyl, unsubstituted or substituted phenyl and substituted or unsubstituted phenyl lower alkyl, wherein phenyl may be substituted by group T; and
R$^{13}$ is hydrogen or lower alkyl.

12. A compound of claim 11 wherein A is represented by formula IIa or IIb wherein p is 0 and q is 1.

13. A compound of claim 11 wherein E is —NH—.

14. A compound of claim 11 wherein R$^7$ is hydrogen, methyl or aminobutyl.

15. A compound of claim 11 wherein L is 2-thiazolyl.

16. A compound of claim 11 wherein R$^6$ and R$^8$ are independently hydroxy, methoxy, ethoxy, phenoxyethoxy, pivaloyloxymethoxy, 1-glyceryl or

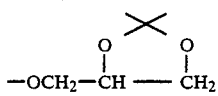

17. An antihypertensive pharmaceutical composition comprising an antihypertensive effective amount of compound of claim 11 together with a pharmaceutically acceptable carrier therefor.

18. A method for reducing blood pressure in hypertensive mammals which comprises administering to a hypertensive mammal a compostiion comprising an antihypertensive effective amount of a compound of claim 11 together with a pharmaceutically acceptable carrier therefor.

19. A compound represented by the formula

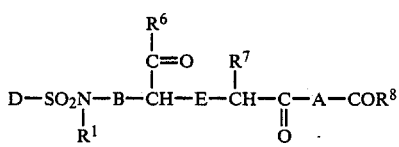

and the pharmaceutically acceptable salts thereof, wherein:

A is

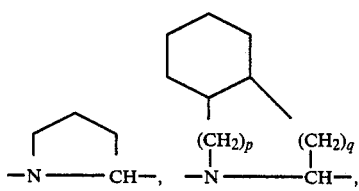

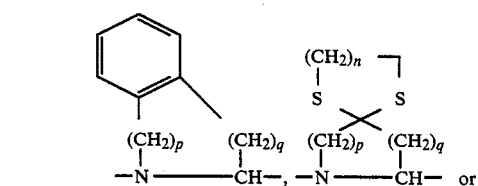

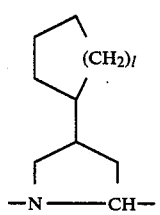

l is 1 or 2;
n is 0 or 1;
p and q are 0, 1 or 2, provided that in structures IIb and IIc the sum of p and q is 1 or 2, and that in formula IId, p is not 0;
B is —J—L—M—;
D is

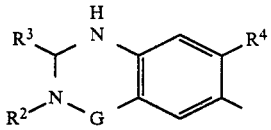

E is —NH—, —O—, —S—, or —CH$_2$—;
G is —SO$_2$—;
J is —(CH$_2$)$_s$— or —((CH$_2$)$_t$—W)—;
L is a 5- or 6-membered heterocyclic radical comprising 3 to 5 carbon atoms and 1 or 2 heteroatoms selected from N, O and S, or a R$^5$-substituted heterocyclic radical;
M is —(CH$_2$)$_u$— or —((CH$_2$)$_t$—X—(CH$_2$)$_v$)—;
W is

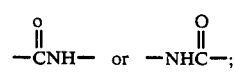

X and Z are independently a chemical bond,

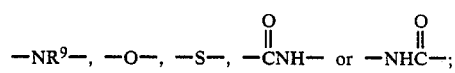

s, u and v are independently 0–5;
t is 1–5;
R$^1$, R$^2$ and R$^9$ are indepently hydrogen, lower alkyl or lower acyl;
R$^3$ is 2-, 3- or 4-pyridylloweralkyl, 2-, 4- or 5-thiazolylloweralkyl, 2-, 4- or 5-1H-imidazolylloweralkyl, 1-imidazolylloweralkyl, 1-morpholinoloweralkyl or hydroxyphenylloweralkyl;
R$^4$ is chlorine or CF$_3$;
R$^5$ is hydrogen, halogen, lower alkyl, lower acyl, lower alkoxy, haloloweralkyl or phenylloweralkyl;
R$^7$ is hydrogen, lower alkyl or aminoloweralkyl;
R$^6$ and R$^8$ are independently hydroxy, alkoxy having from 1 to 8 carbon atoms, benzyl, allyl, R$^{10}$—Q$_r$—(CH$_2$)$_m$—O—, wherein Q is oxygen or sulfur, r is 0 or 1 and m is 2 to 4,

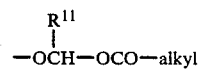

wherein the alkyl has from 3 to 8 carbon atoms,

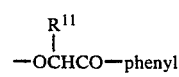

wherein the phenyl may be substituted with group T defined below, 1-glyceryl,

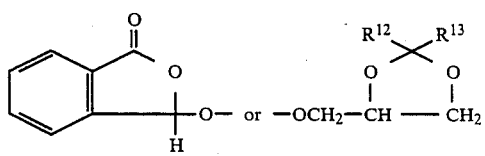

R$^{10}$ is phenyl, substituted phenyl wherein the substituents are chosen from group T, 1-naphthyl or 2-naphthyl; are independently 0–5;

T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;

$R^{11}$ is hydrogen or alkyl having from 1 to 8 carbon atoms;

$R^{12}$ is hydrogen, lower alkyl, unsubstituted or substituted phenyl and substituted or unsubstituted phenyl lower alkyl, wherein phenyl may be substituted by group T; and $R^{13}$ is hydrogen or lower alkyl.

20. A compound of claim 19 wherein A is represented by formula IIa or IIb wherein p is 0 and q is 1.

21. A compound of claim 19 wherein E is —NH—.

22. A compound of claim 19 wherein $R^7$ is hydrogen, methyl or aminobutyl.

23. A compound of claim 19 wherein $R^6$ and $R^8$ are independently hydroxy, methoxy, ethoxy, phenoxyethoxy, pivaloyloxymethoxy, 1-glyceryl or

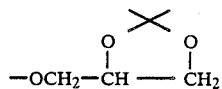

24. An antihypertensive pharmaceutical composition comprising an antihypertensive effective amount of compound of claim 19 together with a pharmaceutically acceptable carrier therefor.

25. A method for reducing blood pressure in hypertensive mammals which comprises administering to a hypertensive mammal a composition comprising an antihypetensive effective amount of a compound of claim 19 together with a pharmaceutically acceptable carrier therefor.

* * * * *